(12) United States Patent
Koehler

(10) Patent No.: US 8,063,218 B2
(45) Date of Patent: Nov. 22, 2011

(54) IMIDAZOPYRIDINE INHIBITORS OF IAP

(75) Inventor: Michael F. T. Koehler, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/520,205

(22) PCT Filed: Dec. 14, 2007

(86) PCT No.: PCT/US2007/087532
§ 371 (c)(1),
(2), (4) Date: Jun. 19, 2009

(87) PCT Pub. No.: WO2008/079735
PCT Pub. Date: Jul. 3, 2008

(65) Prior Publication Data
US 2010/0130539 A1   May 27, 2010

Related U.S. Application Data

(60) Provisional application No. 60/870,821, filed on Dec. 19, 2006.

(51) Int. Cl.
*C07D 491/02* (2006.01)
(52) U.S. Cl. .................................................. 546/121
(58) Field of Classification Search ................ None
See application file for complete search history.

(56) References Cited

U.S. PATENT DOCUMENTS

| | | | |
|---|---|---|---|
| 4,149,003 A | 4/1979 | Carlsson et al. | |
| 4,278,793 A | 7/1981 | Durckheimer et al. | |
| 4,720,484 A | 1/1988 | Vincent et al. | |
| 4,837,165 A | 6/1989 | Hawke | |
| 4,935,494 A | 6/1990 | Miller | |
| 5,411,942 A | 5/1995 | Widmer et al. | |
| 5,559,209 A | 9/1996 | Nishimoto | |
| 6,472,172 B1 | 10/2002 | Deng et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,067,274 B2 | 6/2006 | Fairbrother | |
| 7,244,851 B2 | 7/2007 | Cohen et al. | |
| 2002/0177557 A1 | 11/2002 | Shi | |
| 2003/0157522 A1 | 8/2003 | Boudreault et al. | |
| 2004/0171554 A1 | 9/2004 | Franklin et al. | |
| 2005/0197403 A1 | 9/2005 | Harran et al. | |
| 2005/0214802 A1 | 9/2005 | Fairbrother et al. | |
| 2005/0234042 A1 | 10/2005 | Palermo et al. | |
| 2006/0052311 A1 | 3/2006 | Sharma et al. | |
| 2006/0167066 A1* | 7/2006 | Cohen et al. | 514/365 |

FOREIGN PATENT DOCUMENTS

| | | |
|---|---|---|
| WO | 92/01938 | 2/1992 |
| WO | 94/11026 | 5/1994 |
| WO | 00/00823 | 1/2000 |
| WO | 00/39585 | 7/2000 |
| WO | 02/16402 A2 | 2/2002 |
| WO | 02/16418 A2 | 2/2002 |
| WO | 02/26775 A2 | 4/2002 |
| WO | 02/30959 A2 | 4/2002 |
| WO | 02/096930 A2 | 12/2002 |
| WO | 03/010184 A2 | 2/2003 |
| WO | 03/086470 A2 | 10/2003 |
| WO | 2004/005248 A1 | 1/2004 |
| WO | 2004/007529 A2 | 1/2004 |
| WO | 2004/017991 A1 | 3/2004 |
| WO | 2004/072641 A1 | 8/2004 |
| WO | 2004/106371 A1 | 12/2004 |
| WO | 2005/049853 A2 | 6/2005 |
| WO | 2005/097791 A1 | 10/2005 |
| WO | 2006/020060 A2 | 2/2006 |
| WO | 2006/091972 A2 | 8/2006 |

OTHER PUBLICATIONS

Lawton et al. J. Org. Chem, 1999, 64, 5329-5332.*
Arnt et al., "Synthetic Smac/DIABLO Peptides Enhance the Effects of Chemotherapeutic Agents by Binding XIAP and cIAP1 in Situ" *J. Bio. Chem.* 277(46):44236-44243 (Nov. 2002).
Baktiar, et al., "Transfer of alkoxycarbonyl from alkyl imidazolium-2-carboxylates to benzyl alcohol, a cyclohexanone enamine and diethylamine" *J. Chem. Soc. Perkin Trans. 1* 3:329-243 (Jan. 1994).
Blass, B.E. et al., "Parallel Synthesis and Evaluation of N-(1-Phenylethyl)-5-phenyl-imidazole-2-amines as Na+/K+ ATPase inhibitors" *Bioorg. Med. Chem. Lett.* 10:1543-1545 (2000).
Boatright et al., "A Unified Model for Apical Caspase Activation" *Molecular Cell* 11:529-541 (2003).
Chai Jijie et al., "Structural and biochemical basis of apoptotic activation by SMAC/Diablo" *Nature*, London, GB:Nature Publishing Group vol. 406(6798):855-862 (Aug. 24, 2000).
Chari et al., "Immunoconjugates Containing Novel Maytansinoids: Promising Anticancer Drugs" *Cancer Research* 52:127-131 (Jan. 1992).

(Continued)

*Primary Examiner* — Brandon Fetterolf
*Assistant Examiner* — Anna Pagonakis
(74) *Attorney, Agent, or Firm* — David W Evans; Genentech, Inc.

(57) ABSTRACT

The invention provides novel inhibitors of IAP that are useful as therapeutic agents for treating malignancies where the compounds have the general formula I: wherein Q, $X_1$, $X_2$, Y, Z $R_1$, $R_2$, $R_3$, $R_3'$, $R_4$, $R_4'$, $R_5$, $R_6$, $R_6'$ and n are as described herein.

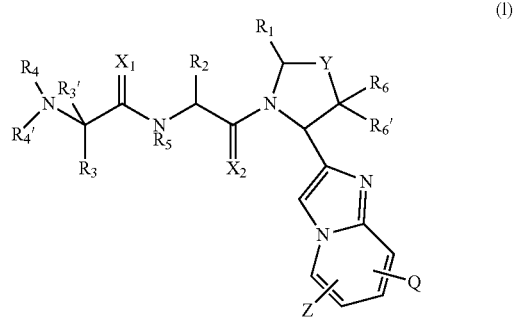

(I)

14 Claims, No Drawings

OTHER PUBLICATIONS

Chen et al., "grim, a novel cell death gene in *Drosophila*" *Genes & Development* 10:1773-1782 (1996).
Christich et al., "The Damage-Responsive *Drosophila* Gene sickle Encodes a Novel IAP Binding Protein Similar to but Distinct from reaper, grim, and hid" *Current Biology* 12:137-140 (2002).
Corey, E.J. et al., "(+)-1(S), 5(R), 8(S)-phenyl-2-azabicyclo[3.3. 0]OCTAN-8-0L N, O-methylboronate (2) and its enantiomer, chiral chemzymes which serve as catalysts for their own enantioselective synthesis" *Tetrahedron Letters* 30(41):5547-5550 (1989).
Crook et al., "An Apoptosis-Inhibiting Baculovirus Gene with a Zinc Finger-Like Motif" *Journal of Virology* 67(4):2168-2174 (Apr. 1993).
Derossi et al., "Trojan Peptides: The Penetratin System for Intracellular Delivery" *Trends Cell Biol.* 8:84-87 (Feb. 1998).
Deveraux et al., "Endogenous Inhibitors of Caspases" *J. Clin. Immunol.* 19(6):388-398 (1999).
Deveraux et al., "IAPs Block Apoptotic Events Induced by Caspase-8 and Cytochrome c by Direct Inhibition of Distinct Caspases" *EMBO Journal* 17(8):2215-2223 (1998).
Deveraux, Q. & Reed, J., "IAP family proteins-suppressors of apoptosis" *Genes Dev* 13:239-252 (1999).
Duckett et al., "A Conserved Family of Cellular Genes Related to the Baculovirus iap Gene and Encoding Apoptosis Inhibitors" *EMBO Journal* 15(11):2685-2694 (1996).
Fong et al., "Expression and genetic analysis of XIAP-associated factor 1 (XAF1) in cancer cell lines" *Genomics* 70:113-122 (2000).
Franklin et al., "Structure and Function Analysis of Peptide Antagonists of Melanoma Inhibitor of Apoptosis (ML-IAP)" *Biochemistry* 42:8223-8231 (2003).
Fulda et al., "Smac Agonists Sensitize for Apo2L/TRAIL- or Anticancer Drug-Induced Apoptosis and Induce Regression of Malignant Glioma in Vivo" *Nature Medicine* 8(8):808-815 (Aug. 2002).
Goyal et al., "Induction of apoptosis by *Drosophila* reaper, hid and grim through inhibition of IAP function" *Embo Journal* 19:589-597 (2000).
Grether et al., "The head involution defective gene of *Drosophila melanogaster* functions in programmed cell death" *Genes Dev* 9:1694-1708 (1995).
Guo et al., "Ectopic Overexpression of Second Mitochondria-Derived Activator of Caspases (Smac/DIABLO) or Cotreatment with N-Terminus of Smac/DIABLO Peptide Potentiates Epothilone B Derivative-(BMS 247550) and Apo-2L/TRAIL-Induced Apoptosis" *Blood* 99:3419-3426 (2002).
Hinds et al., "Solution Structure of a Baculoviral Inhibitor of Apoptosis (IAP) Repeat" *Nat. Struct. Biol.* 6:648-651 (Jul. 1999).
Hu et al., "Antisense oligonucleotides targeting XIAP induce apoptosis and enhance chemotherapeutic activity against human lung cancer cells in vitro and in vivo" *Clin. Cancer Res* 9(7):2826-2836 (2003).
Jones et al., "Improved methods for building protein models in electron density maps and the location of errors in these models" *Acta Cryst.* A47:110-119 (1991).
Keating et al., "Putting the Pieces Together: Contribution of Fluorescence Polarization Assays to Small Molecule Lead Optimization" *Proceedings of SPIE: In Vitro Diagnostic Instrument.*, Cohn, G.E. ed. vol. 3913:128-137 (2000).
Kipp et al., "Molecular Targeting of Inhibitor of Apoptosis Proteins Based on Small Molecule Mimics of Natural Binding Partners." *Biochemistry* 41:7344-7349 (2002).
Kolb et al., "Use of a novel homogeneous fluorescent technology in high throughput screening" *J Biomolecular Screening* 1(4):203-210 (1996).
Kolb et al., "Use of a Novel Homogeneous Fluorescent Technology in High Throughput Screening" *J. Biomol. Screening* 1(4):203-210 (1996).
LaCasse et al., "The inhibitors of apoptosis (IAPs) and their emerging role in cancer" *Oncogene* 17(25):3247-3259 (1998).
Lawton, et al., "A Bioactive Modified Peptide, Aeruginosamide, Isolated from the Cyanbacterium Microcytis aeruginosa" *J. Org. Chem.* 64:5329-5332 (Jun. 24, 1999).

Lin et al., "Resistance of bone marrow-derived macrophages to apoptosis is associated with the expression of X-linked inhibitor of apoptosis protein in primary cultures of bone marrow cells" *Biochemical Journal* 353:299-306 (2001).
Lin, Li et al., "A small molecule Smac mimic potentiates TRAIL- and TNF alpha-mediated cell death" *Science* 305:1471-1474 (2004).
Liston et al., "Suppression of apoptosis in mammalian cells by NAIP and a related family of IAP genes" *Nature* 379:349-353 (1996).
Liu et al., "Eradication of Large Colon Tumor Xenografts by Targeted Delivery of Maytansinoids." *Proc. Natl. Acad. Sci. USA* 93:8618-8623 (1996).
Liu et al., "Structural Basis for Binding of Smac/DIABLO to the XIAP BIR3 Domain" *Nature* 408:1004-1008 (Dec. 2000).
Masuda et al., "Studies on mesoionic compounds. Part 11. Alkylation of 5-acylamino-1,2,3-thiadiazoles" *J. Chem. Soc. Perkin. Trans. 1* 5:1591-1595 (1981).
Murray, D. et al., "Synthetic peptide substrates for the erythrocyte protein carboxyl methyltransferase" *J Biol. Chem.* 259(17):10722-10732 (1984).
Murshudov et al., "Refinement of Macromolecular Structures by the Maximum-Likelihood Method" *Acta Cryst.* D53:240-255 (1997).
Ng and Bonavida, "X-Linked Inhibition of Apoptosis (XIAP) Blocks Apo2 Ligand/Tumor Necrosis Factor-Related Apoptosis-Inducing Ligand-Mediated Apoptosis of Prostate Cancer Cells in the Presence of . . . " *Mol. Cancer Ther.* 12:1051-1058 (2002).
Pan et al., "An Antagonist Decoy Receptor and a Death-Domain Containing Receptor for TRAIL" *Science* 277:815-818 (Aug. 1997).
Perrakis et al, "ARP/wARP and molecular replacement" *Acta Crystallographica* D57:1445-1450 (2001).
Prochiantz, A., "Getting Hydrophilic Compounds into Cells: Lessons from Homeopeptides" *Curr. Opinion Neurobiol.* 6(5):629-634 (1996).
Riedl et al., "Structural Basis for the Inhibition of Caspase-3 by XIAP" *Cell* 104:791-800 (Mar. 2001).
Salvesen and Nagase, "Determination of protease mechanism" *Proteolytic enzymes: A practical approach*, R.J. Beynon and J.S. Bond, Oxford, IRL Press pp. 83-104 (1989).
Sanna M et al., "IAP suppression of apoptosis involves distinct mechanisms: the TAK1/JNK1 signaling cascade and caspase inhibition" *Mol Cell Biol.* 22(6):1754-1766 (Mar. 2002).
Sasaki et al., "Down-regulation of X-linked inhibitor of apoptosis protein induces apoptosis in chemoresistant human ovarian cancer cells" *Cancer Research* 60(20):5659-5666 (2000).
Shiozaki et al., "Mechanism of XIAP-Mediated Inhibition of Caspase-9" *Molecular Cell* 11:519-527 (2003).
Shuker et al., "Discovering High-Affinity Ligands for Proteins: SAR by NMR" *Science* 274:1531-1534 (Nov. 1996).
Sidhu et al., "Phage Display for Selection of Novel Binding Peptides" *Methods Enzymology* 328:333-363 (2000).
Srinivasula et al., "A conserved XIAP-interaction motif in caspase-9 and Smac/DIABLO regulates caspase activity and apoptosis" *Nature* 410:112-116 (2001).
Srinivasula et al., "sickle, a Novel *Drosophila* Death Gene in the reaper/hid/grim Region, Encodes an IAP-Inhibitory Protein" *Current Biology* 12:125-130 (2002).
Stark, "Sequential degradation of peptides from their carboxyl termini with ammonium thiocyanate and acetic anhydride" *Biochemistry* 7(5):1796-1807 (1968).
Sun et al., "NMR Structure and Mutagenesis of the Inhibitor-of-Apoptosis Protein XIAP" *Nature* 401:818-822 (Oct. 1999).
Sun et al., "NMR Structure and Mutagenesis of the Third Bir Domain of the Inhibitor of Apoptosis Protein XIAP" *Journal of Biological Chemistry* 275:33777-33781 (Oct. 2000).
Takahashi et al., "A Single BIR Domain of XIAP Sufficient for Inhibiting Caspases" *The Journal of Biological Chemistry* 273:7787-7790 (1998).
Tamm et al., "Expression and prognostic significance of IAP-family genes in human cancers and myeloid leukemias" *Clin. Cancer Res.* 6(5):1796-1803 (2000).
Tenev et al., "Jafrac2 is an IAP antagonist that promotes cell death by liberating Dronc from DIAP1" *Embo Journal* 21:5118-5129 (2002).

Thompson, "Apoptosis in the Pathogenesis and Treatment of Disease" *Science* 267:1456-1462 (1995).

Vippagunta, et al., "Crystalline solids" *Advanced Drug Delivery Reviews* 48:3-26 (2001).

Vucic D et al., "Engineering ML-IAP to produce an extraordinarily potent caspase 9 inhibitor: implications for Smac-dependent anti-apoptotic activity of ML-IAP" *Biochemical Journal* 385(Part 1):11-20 (Jan. 2005).

Vucic et al., "ML-IAP, A Novel Inhibitor of Apoptosis that is Preferentially Expressed in Human Melanomas" *Current Bio.* 10:1359-1366 (Oct. 2000).

Vucic et al., "SMAC Negatively Regulates the Anti-apoptotic Activity of Melanoma Inhibitor of Apoptosis (ML-IAP)" *The Journal of Biological Chemistry* 277:12275-12279 (2002).

White et al., "Genetic Control of Programmed Cell Death in *Drosophila*" *Science* 264:677-683 (1994).

Wing et al., "*Drosophila* sickle Is a Novel grim-reaper Cell Death Activator" *Current Biology* 12:131-135 (2002).

Wu et al., "Structural Analysis of a Functional DIAP1 Fragment Bound to Grim and Hid Peptides" *Mol. Cell.* 8:95-104 (Jul. 2001).

Wu et al., "Structural Basis of IAP Recognition by Smac/DIABLO" *Nature* 408:1008-1012 (Dec. 2000).

Yang et al., "Predominant suppression of apoptosome by inhibitor of apoptosis protein in non-small cell lung cancer H460 cells: therapeutic effect of a novel polyarginine-conjugated smac peptide" *Cancer Research* 63(4):831-837 (2003).

* cited by examiner

IMIDAZOPYRIDINE INHIBITORS OF IAP

CROSS-REFERENCE TO RELATED APPLICATIONS

This application claims priority under 35 U.S.C. §119(e) to U.S. Ser. No. 60/870,821, filed Dec. 19, 2006, which is incorporated by reference in its entirety.

FIELD OF THE INVENTION

The present invention relates to organic compounds useful for therapy and/or prophylaxis in a mammal, and in particular to inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563): 349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406: 855-862, Liu et al., (2000) Nature 408:1004-1008, Wu et al., (2000) Nature 408 1008-1012).

SUMMARY OF THE INVENTION

In one aspect of the present invention there is provided novel inhibitors of IAP proteins having the general formula (I)

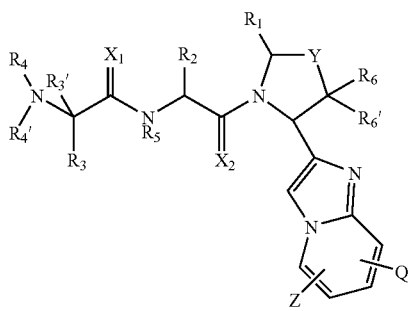

wherein
$X_1$ and $X_2$ are each independently O or S;
Y is a bond, $(CR_7R_7)_m$, or S;
Z is H, halogen, hydroxyl, carboxyl, amino, nitro, cyano, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, $S(O)_2$, —$N(R_8)$—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—;
Q is H, halogen, hydroxyl, carboxyl, amino, nitro, cyano, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, $S(O)_2$, —$N(R_8)$—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—;
$R_1$ is H, OH or alkyl; or $R_1$ and $R_2$ together form a 5-8 member heterocycle;
$R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, acyl, alkoxy, alkylthio, sulfonyl, amino and nitro, wherein said alkyl, acyl, alkoxy, alkylthio and sulfonyl are optionally substituted with hydroxy, mercapto, halogen, amino, alkoxy, hydroxyalkoxy and alkoxyalkoxy;
$R_3$ is H or alkyl optionally substituted with halogen or hydroxyl; or $R_3$ and $R_4$ together form a 3-6 heterocycle;
$R_3'$ is H, or $R_3$ and $R_3'$ together form a 3-6 carbocycle;
$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle;
$R_5$ is H or alkyl;
$R_6$, and $R_6'$ are each independently H, alkyl, aryl or aralkyl;
$R_7$ is H, cyano, hydroxyl, mercapto, halogen, nitro, carboxyl, amidino, guanidino, alkyl, a carbocycle, a heterocycle or —U—V; wherein U is —O—, —S—, —S(O)—, $S(O)_2$, —$N(R_8)$—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)— and V is alkyl, a carbocycle or a heterocycle; and wherein one or more $CH_2$ or CH groups of an alkyl is optionally replaced with —O—, —S—, —S(O)—, $S(O)_2$, —$N(R_8)$—, —C(O)—$NR_8$—, —$NR_8$—C(O)—, —$SO_2$—$NR_8$—, —$NR_8$—$SO_2$—, —$NR_8$—C(O)—$NR_8$—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle;
$R_8$ is H, alkyl, a carbocycle or a heterocycle wherein one or more $CH_2$ or CH groups of said alkyl is optionally replaced with —O—, —S—, —S(O)—, $S(O)_2$, —$N(R_8)$, or —C(O)—; and said alkyl, carbocycle and heterocycle is optionally substituted with hydroxyl, alkoxy, acyl, halogen, mercapto, oxo (=O), carboxyl, acyl, halo-substituted alkyl, amino, cyano nitro, amidino, guanidino an optionally substituted carbocycle or an optionally substituted heterocycle; and
m is 0 to 4.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon chains such as "alkenylamino" and "alkynylamino." Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one, for example two, three or four substituents which may be the same or different. Examples of substituents are, unless otherwise defined, halogen, amino, hydroxyl, protected hydroxyl, mercapto, carboxy, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" means the group —C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular amidine is the group —NH—C(NH)—NH$_2$.

"Amino" means primary (i.e. —NH$_2$), secondary (i.e. —NRH) and tertiary (i.e. —NRR) amines in which R is H, alkyl, a carbocycle, a heterocycle, carbocycle-substituted alkyl or heterocycle-substituted alkyl wherein the alkyl, alkoxy, carbocycle and heterocycle are as defined herein. Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Particular carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" means the group —NH—C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles are morpholinyl (morpholino), pyrrolidinyl, oxiranyl, oxetanyl, tetrahydropyranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substittuted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the binding of IAP proteins to caspase proteins or which reduces or prevents the inhibition of apoptosis by an IAP protein. Alternatively, "inhibitor" means a compound which prevents the binding interaction of X-IAP with caspases or the binding interaction of ML-IAP with SMAC.

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfonyl" means a $SO_2$—R group in which R is H, alkyl, a carbocycle, a heterocycle, carbocycle-substituted alkyl or heterocycle-substituted alkyl wherein the alkyl, alkoxy, carbocycle and heterocycle are as defined herein. Particular sulfonyl groups are alkylsulfonyl (i.e. $SO_2$-alkyl), for example methylsulfonyl; arylsulfonyl, for example phenylsulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The present invention provides novel compounds having the general formula I:

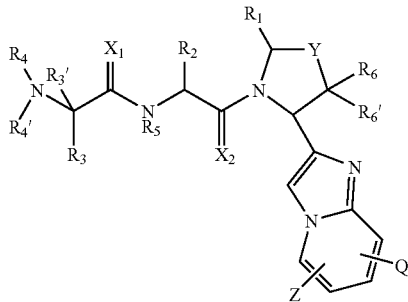

I wherein Q, $X_1$, $X_2$, Y, Z, $R_1$, $R_2$, $R_3$, $R_3'$, $R_4$, $R_4'$, $R_5$, $R_6$, $R_6'$ and n are as described herein. Compounds of the invention include salts, solvates and polymorphs thereof unless otherwise specified.

$X_1$ and $X_2$ are each independently O or S. In a particular embodiment, $X_1$ and $X_2$ are both O. In another particular embodiment $X_1$ and $X_2$ are both S. In another particular embodiment, $X_1$ is S while $X_2$ is O. In another particular embodiment, $X_1$ is O while $X_2$ is S.

Y is a bond, $(CR_7R_7)_m$ or S. In an embodiment Y is a bond, $(CR_7R_7)_m$, O or S; wherein m is 1 or 2 and $R_7$ is as defined herein or is H, halogen, alkyl, aryl, aralkyl, amino, arylamino, alkylamino, aralkylamino, alkoxy, aryloxy or aralkyloxy. In a particular embodiment, Y is $(CHR_7)_m$, O or S; wherein m is 1 or 2 and $R_7$ is H, halogen, alkyl, aryl, aralkyl, amino, arylamino, alkylamino, aralkylamino, alkoxy, aryloxy or aralkyloxy. In a particular embodiment, Y is $CH_2$. In a particular embodiment m is 1. In a particular embodiment Y is a bond. In a particular embodiment m is 1 and Y is $CHR_7$ wherein $R_7$ is aralkyloxy, for example benzyloxy. In a particular embodiment m is 1 and Y is $CHR_7$ wherein $R_7$ is F. In a particular embodiment m is 1 and Y is $CHR_7$ wherein $R_7$ is aralkylamino, for example benzylamino. In another particular embodiment Y is O. In another particular embodiment Y is S.

Z is H, halogen, hydroxyl, carboxyl, amino, nitro, cyano, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—. In an embodiment Z is H, halogen, hydroxyl, carboxyl, amino, nitro, alkyl, a carbocycle or a heterocycle wherein said alkyl, carbocycle and heterocycle are optionally substituted with halogen, hydroxyl, carboxyl, amino, and nitro. In an embodiment Z is H, halogen or alkyl. In an embodiment Z is H. In an embodiment Z is alkyl, for example methyl, ethyl, propyl and isopropyl. In an embodiment Z is phenyl or naphthyl.

Q is H, halogen, hydroxyl, carboxyl, amino, nitro, cyano, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—. Substituents of the "optionally substituted alkyl", "optionally substituted carbocycle" and "optionally substituted heterocycle" are substituted as the foregoing alkyl, carbocycle and heterocycle groups in Q. In a particular embodiment substituents of such "optionally substituted alkyl" are hydroxyl, alkoxy, acyl, halogen, mercapto, oxo, carboxyl, acyl, amino, cyano, nitro, amidino and guanidino. In a particular embodiment such optionally substituted carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment Q is a carbocycle or heterocycle optionally substituted with halogen, amino, oxo, alkyl, a carbocycle or a heterocycle; wherein one or more $CH_2$ or CH groups of an alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$-, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—; and wherein said alkyl, carbocycle or heterocycle is optionally substituted with halogen, amino, hydroxyl, mercapto, carboxyl, alkoxy, alkoxyalkoxy, hydroxyalkoxy, alkylthio, acyloxy, acyloxyalkoxy, alkylsulfonyl, alkylsulfonylalkyl, alkylsulfinyl, and alkylsulfinylalkyl. In a particular embodiment Q is a carbocycle or a heterocycle as defined herein which is optionally substituted as described herein while Z is selected from the group consisting of H, halogen, carboxyl, amino, nitro and cyano. In a particular embodiment Q is aryl or heteroaryl while Z is selected from the group consisting of H, halogen, carboxyl, amino, nitro and cyano. In a particular embodiment Z is H. In another particular embodiment, such other instances of Z is H, halogen or alkyl.

In a particular embodiment, Q is a carbocycle or heterocycle selected from the group consisting of III-1-III-16

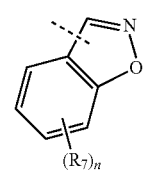

III-1

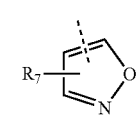

III-2

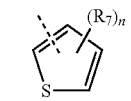

III-3

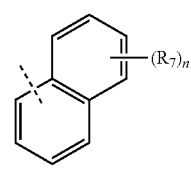

III-4

III-5 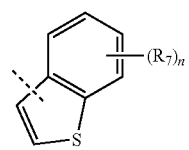

III-6 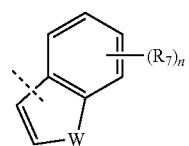

III-7 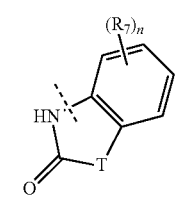

III-8 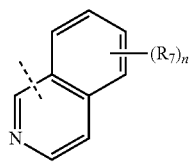

III-9 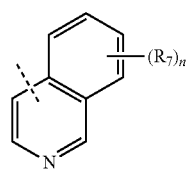

III-10 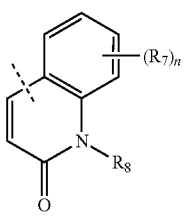

III-11 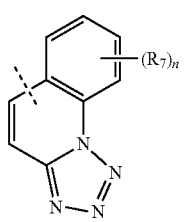

III-12 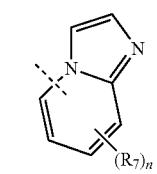

III-13 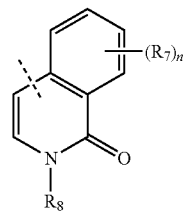

III-14 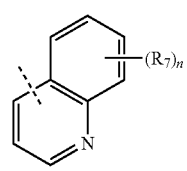

III-15 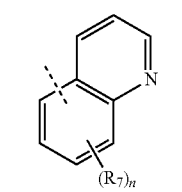

III-16 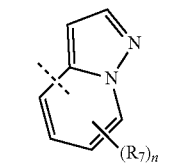

wherein n is 1-4, for example 1-3, for example 1-2, for example 1; T is O, S, $NR_8$ or $CR_7R_7$; W is O, $NR_8$ or $CR_7R_7$; and $R_7$ and $R_8$ are as defined herein. In an embodiment, Q has the general formulae III-1 to III-16 while Z is selected from the group consisting of H, halogen, carboxyl, amino, nitro and cyano. In a particular embodiment Z is H. In another particular embodiment, Z is H, halogen or alkyl.

In a particular embodiment, Q is a carbocycle or heterocycle selected from the group consisting of IIIa-IIIs:

IIIa 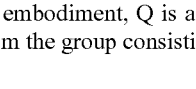

IIIb 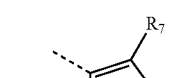

IIIc 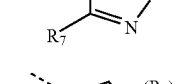

IIId 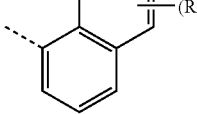

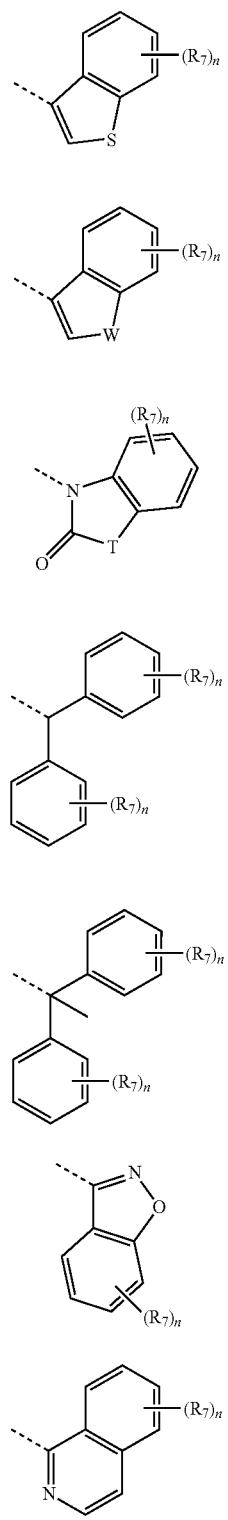
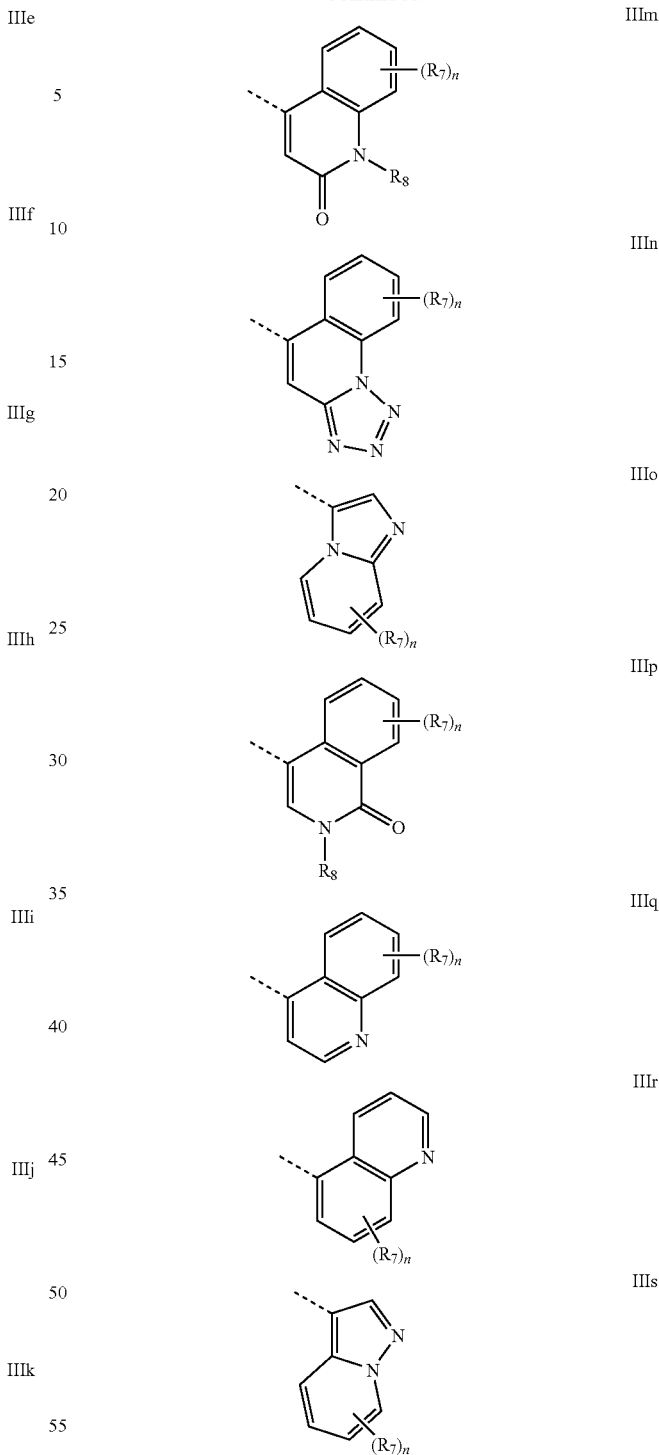

wherein n is 1-4, for example 1-3, for example 1-2, for example 1; T is O, S, NR$_8$ or CR$_7$R$_7$; W is O, NR$_8$ or CR$_7$R$_7$; and R$_7$ and R$_8$ are as defined herein. In a particular embodiment Q is any one of IIIa-IIIi wherein R$_8$ is H and R$_7$ is selected from the group consisting of H, F, Cl, Me, methoxy, hydroxyethoxy, methoxyethoxy, acetoxyethoxy, methylsulfonyl methylsulfonylmethyl, phenyl and morpholin-4-yl. In another particular embodiment Q is IIId. In a particular embodiment Q is IIId which is substituted at the 4-position with R$_7$. In another particular embodiment Q is IIId which is substituted at the 5-position with $R_7$. In a particular embodiment Q is F, Me, iPr, phenyl, phenyl substituted as follows: 2-Cl, 3-Cl, 4-Cl, 2-F, 3-F or 4-F substituted, benzyl, pyrid-3-yl or pyrid-4-yl. In an embodiment, Q has the general formulae IIIa to IIIs while Z is selected from the group consisting of H, halogen, carboxyl, amino, nitro and cyano. In a particular embodiment Z is H. In another particular embodiment, Z is H, halogen or alkyl.

$R_1$ is H, OH or alkyl; or $R_1$ and $R_2$ together form a 5-8 member heterocycle. In a particular embodiment, $R_1$ is H. In a particular embodiment, $R_1$ and $R_2$ together form a 6-member ring. In a particular embodiment, $R_1$ and $R_2$ together form a 7-member ring. In another particular embodiment, $R_1$ and $R_2$ together form an 8-member ring. In another particular embodiment, $R_1$ and $R_2$ together form a 7-member ring while Y is S. In another particular embodiment, $R_1$ is H, while Y is $CH_2$. In another particular embodiment, $R_1$ is H, while Y is S. In another particular embodiment, $R_1$ is H, while Y is O.

$R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, acyl, alkoxy, alkylthio, sulfonyl, amino and nitro, wherein said alkyl, acyl, alkoxy, alkylthio and sulfonyl are optionally substituted with hydroxy, mercapto, halogen, amino, alkoxy, hydroxyalkoxy and alkoxyalkoxy. In an embodiment, $R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, alkoxy, alkylthio, sulfonyl, amino and nitro. In a particular embodiment $R_2$ is alkyl, a carbocycle, carbocyclylalkyl, a heterocycle or heterocyclylalkyl each optionally substituted with halogen, hydroxyl, oxo, mercapto, thione, carboxyl, alkyl, haloalkyl, alkoxy, acyl, alkylthio, acyl, hydroxyacyl, methoxyacyl, sulfonyl, amino and nitro. In an embodiment $R_2$ is alkyl, a carbocycle, carbocyclylalkyl, a heterocycle or heterocyclylalkyl each optionally substituted with halogen, hydroxyl, mercapto, carboxyl, alkyl, alkoxy, acyl, amino and nitro. In a particular embodiment $R_2$ is alkyl, cycloalkyl, cycloalkylalkyl, aryl, aralkyl, a heterocycle or heterocyclylalkyl. In a particular embodiment $R_2$ is alkyl, cycloalkyl or a heterocycle. In a particular embodiment $R_2$ is selected from the group consisting of t-butyl, isopropyl, cyclohexyl, tetrahydropyran-4-yl, N-methylsulfonylpiperidin-4-yl, tetrahydrothiopyran-4-yl, tetrahydrothiopyran-4-yl (in which the S is in oxidized form SO or $SO_2$), cyclohexan-4-one, 4-hydroxycyclohexane, 4-hydroxy-4-methylcyclohexane, 1-methyl-tetrahydropyran-4-yl, 2-hydroxyprop-2-yl, but-2-yl, thiophen-3-yl, piperidin-4-yl, N-acetylpiperidin-4-yl, N-hydroxyethylpiperidin-4-yl, N-(2-hydroxyacetyl)piperidin-4-yl, N-(2-methoxyacetyl)piperidin-4-yl, pyridin-3-yl, phenyl, tetrahydrofuran-2-yl-carbonyl, methoxyethanone, 2-methoxyethoxyethanone and 1-hydroxyeth-1-yl. In an embodiment of the invention $R_2$ is t-butyl, isopropyl, cyclohexyl, cyclopentyl, phenyl or tetrahydropyran-4-yl. In a particular embodiment, $R_2$ is phenyl. In a particular embodiment, $R_2$ is cyclohexyl. In another embodiment $R_2$ is tetrahydropyran-4-yl. In another particular embodiment, $R_2$ is isopropyl (i.e. the valine amino acid side chain). In another particular embodiment, $R_2$ is t-butyl. In a particular embodiment $R_2$ is oriented such that the amino acid, or amino acid analogue, which it comprises is in the L-configuration.

$R_3$ is H or alkyl optionally substituted with halogen or hydroxyl; or $R_3$ and $R_4$ together form a 3-6 heterocycle. In an embodiment $R_3$ is H or alkyl; or $R_3$ and $R_4$ together form a 3-6 heterocycle. In an embodiment $R_3$ is H or methyl, ethyl, propyl or isopropyl. In a particularly particular embodiment $R_3$ is H or methyl. In another particular embodiment $R_3$ is methyl. In another particular embodiment $R_3$ is fluoromethyl. In another particular embodiment, $R_3$ is ethyl. In another particular embodiment $R_3$ is hydroxyethyl. In a particular embodiment $R_3$ is fluoromethyl. In a particular embodiment $R_3$ is hydroxyethyl. In another embodiment $R_3$ is oriented such that the amino acid, or amino acid analogue, which it comprises is in the L-configuration. In a particular embodiment $R_3$ and $R_4$ together with the atoms from which they depend form a 3-6 heterocycle. In a particular embodiment $R_3$ and $R_4$ together form an azetidine ring. In a particular embodiment $R_3$ and $R_4$ together form a pyrrolidine.

$R_3'$ is H, or $R_3$ and $R_3'$ together form a 3-6 carbocycle. In an embodiment, $R_3'$ is H. In another embodiment $R_3$ and $R_3'$ together form a 3-6 carbocycle, for example a cyclopropyl ring. In a particular embodiment $R_3$ and $R_3'$ are both methyl.

$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle. In an embodiment $R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro; or $R_4$ and $R_4'$ together form a heterocycle. In a particular embodiment $R_4$ and $R_4'$ together form a heterocycle, for example an azetidine ring, or a pyrrolidine ring. In a particular embodiment $R_4$ and $R_4'$ are both H. In another particular embodiment $R_4$ is methyl and $R_4'$ is H. In a particular embodiment one of $R_4$ and $R_4'$ is hydroxyl (OH) while the other is H. In another embodiment, one of $R_4$ and $R_4'$ is amino, such as $NH_2$, NHMe and NHEt, while the other is H. In a particular embodiment, $R_4'$ is H and $R_4$ is H, allyl, aryl, aralkyl, cycloalkyl, cycloalkylalkyl, heteroaryl or heteroarylalkyl. In a particular embodiment $R_4$ is a group selected from the group consisting of:

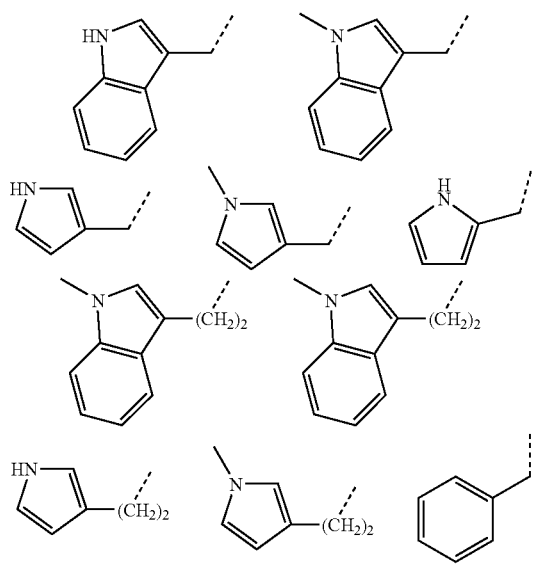

-continued

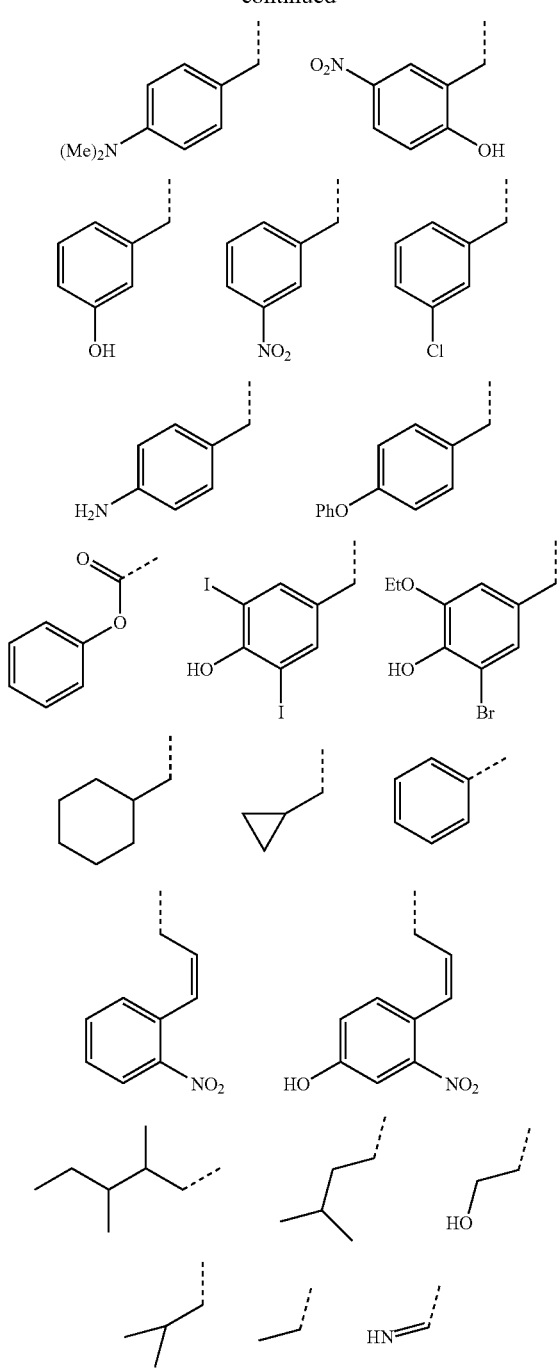

$R_5$ is H or alkyl. In a particular embodiment, $R_5$ is H or methyl. In a particular embodiment, $R_5$ is H. In another particular embodiment, $R_5$ is methyl.

$R_6$, and $R_6'$ are each independently H, alkyl, aryl or aralkyl. In a particular embodiment, $R_6$ is alkyl, for example methyl. In another particular embodiment, $R_6$ is aryl, for example phenyl. In another particular embodiment $R_6$ is aralkyl, for example benzyl. In a particular embodiment $R_6$ and $R_6'$ are the same, for example both alkyl, e.g. both methyl. In another particular embodiment $R_6$ is methyl and $R_6'$ is H.

$R_7$ in each occurrence is independently H, cyano, hydroxyl, mercapto, halogen, nitro, carboxyl, amidino, guanidino, alkyl, a carbocycle, a heterocycle or —U—V; wherein U is —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)— and V is alkyl, a carbocycle or a heterocycle; and wherein one or more CH$_2$ or CH groups of an alkyl is optionally replaced with —O—, —S—, —S(O)—, S(O)$_2$, —N(R$_8$)—, —C(O)—, —C(O)—NR$_8$—, —NR$_8$—C(O)—, —SO$_2$—NR$_8$-, —NR$_8$—SO$_2$-, —NR$_8$—C(O)—NR$_8$—, —NR$_8$—C(NH)—NR$_8$—, —NR$_8$—C(NH)—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano, nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In an embodiment $R_7$ is H, halogen, alkyl, haloalkyl, aryl, aralkyl, amino, arylamino, alkylamino, aralkylamino, alkoxy, alkoxyalkoxy, aryloxy or aralkyloxy.

$R_8$ is H, alkyl, a carbocycle or a heterocycle wherein one or more CH$_2$ or CH groups of said alkyl is optionally replaced with —O—, —S—, —S(O)—, S(O)$_2$, —N(R$_8$), or —C(O)—; and said alkyl, carbocycle and heterocycle is optionally substituted with hydroxyl, alkoxy, acyl, halogen, mercapto, oxo (=O), carboxyl, acyl, halo-substituted alkyl, amino, cyano nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment $R_8$ is H, alkyl, or acyl. In an embodiment $R_8$ is methyl. In another embodiment $R_8$ is acetyl. In a particular embodiment $R_8$ is H. In an embodiment $R_7$ is H, halogen, amino, hydroxyl, carboxyl, alkyl, haloalkyl or aralkyl. In a particular embodiment $R_7$ is halogen, for example Cl or F. In a particular embodiment $R_7$ is H. It is understood that substitutions defined for $R_7$ and $R_8$ as well as all other variable groups herein are subject to permissible valency.

m is 0 to 4. In an embodiment m is 0. In an embodiment m is 1. In an embodiment m is 2. In an embodiment m is 3. In an embodiment m is 4.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. In a particular embodiment, compounds of the invention have the following stereochemical configuration of formula I'

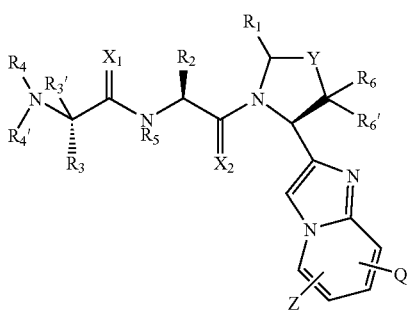

wherein $X_1, X_2, Y, Z, Q R_1, R_2, R_3, R_4, R_4', R_5, R_6$ and $R_6'$ are as described herein.

In particular embodiments, compounds of the invention have the general formula IIa-IId

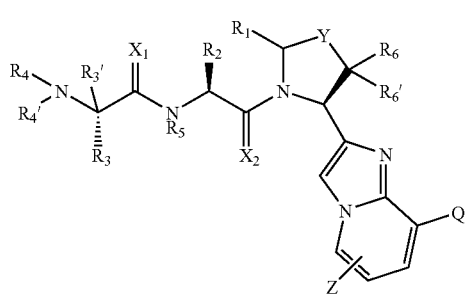

IIa

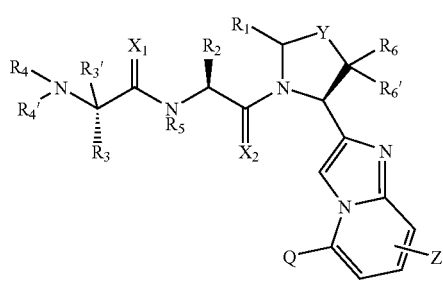

IIb

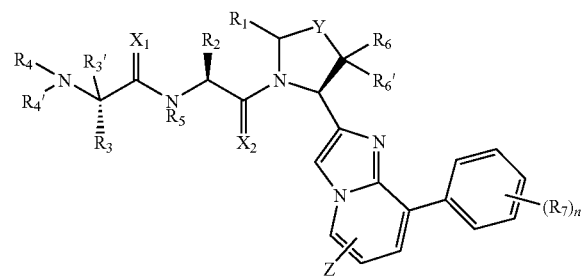

IIc

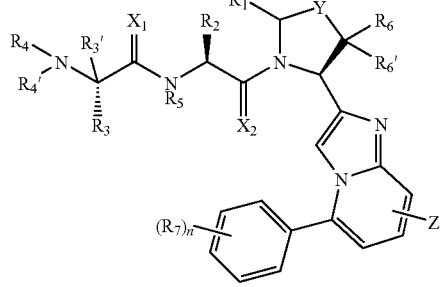

IId wherein $X_1, X_2, Y, Z, Q R_1, R_2, R_3, R_4, R_4', R_5, R_6, R_6'$ and $R_7$ are as described herein.

The invention also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:

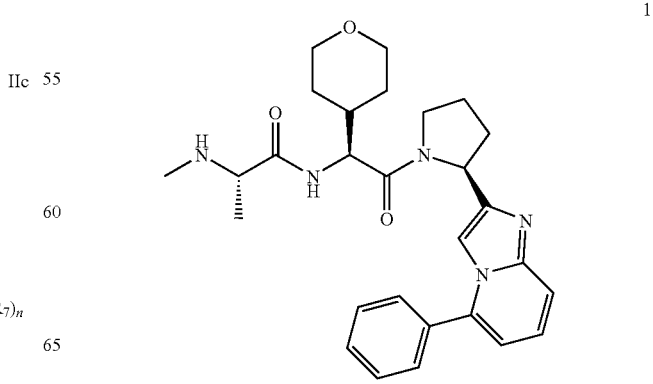

1

2
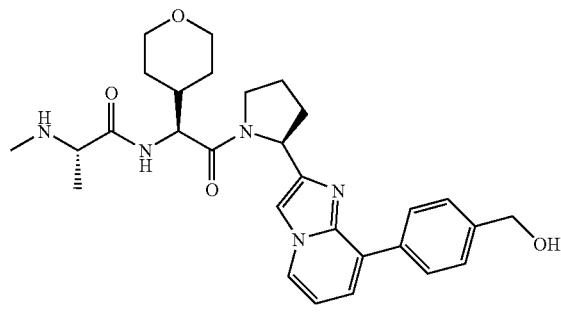
3
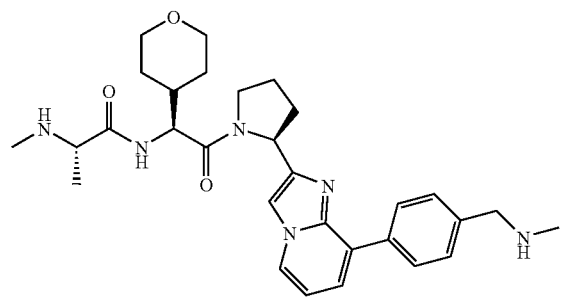
4
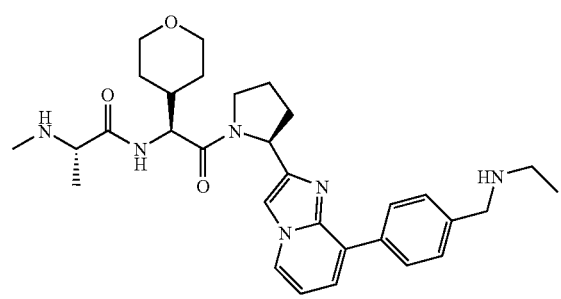
5
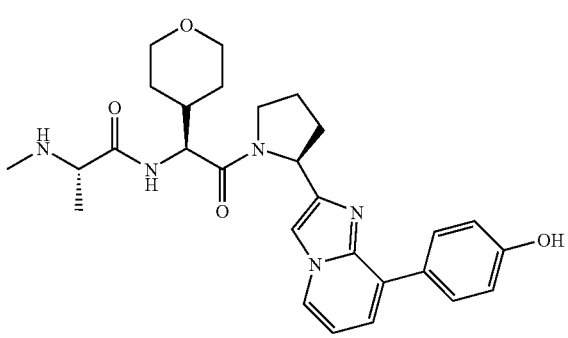
6
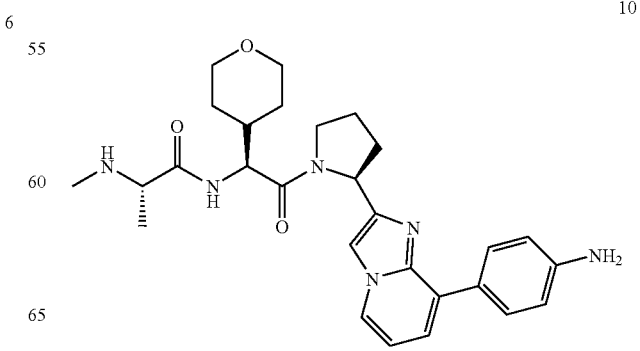
7
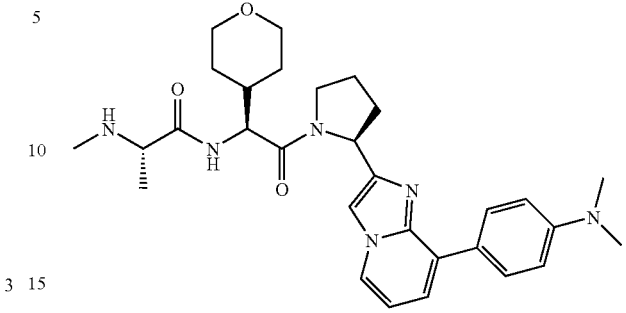
8
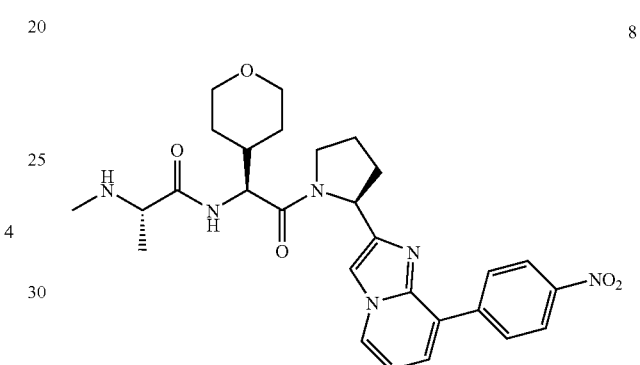
9
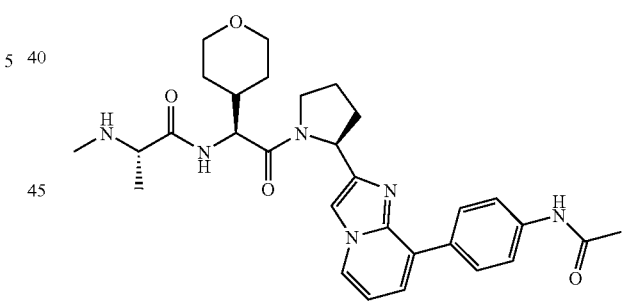
10

25
-continued
11
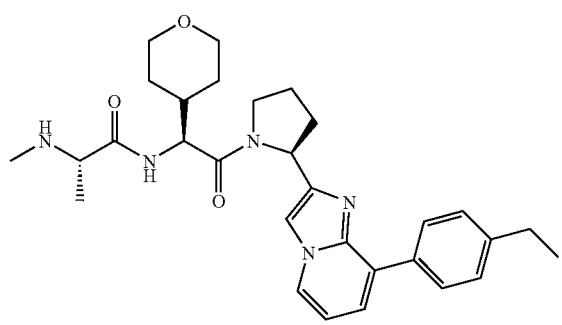
12
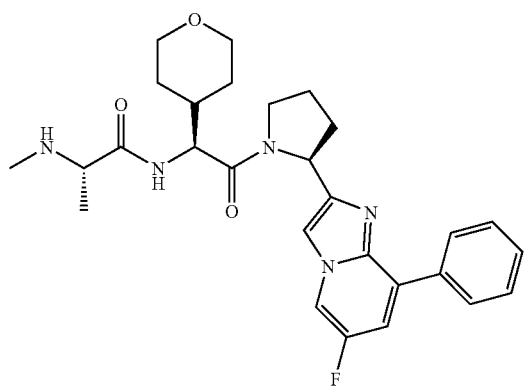
13
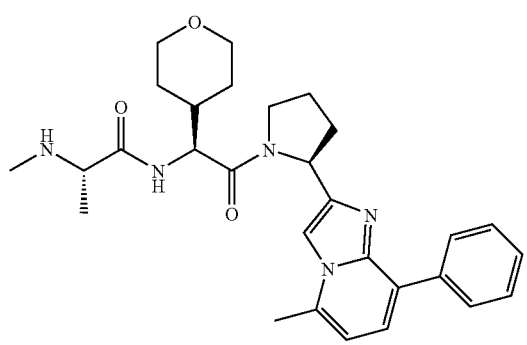
14
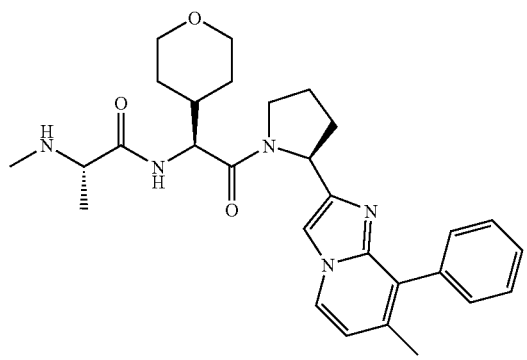
26
-continued
15
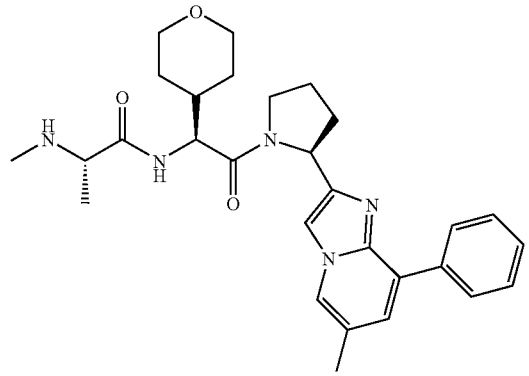
16
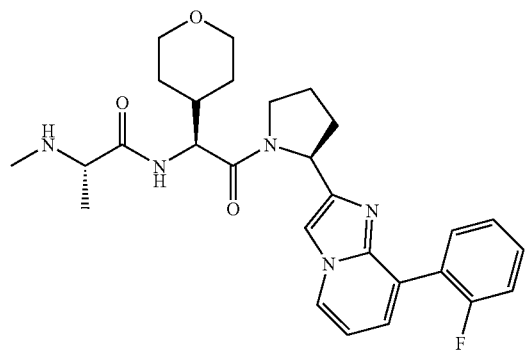
17
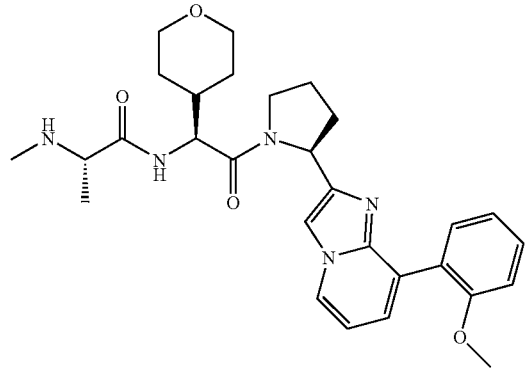
18
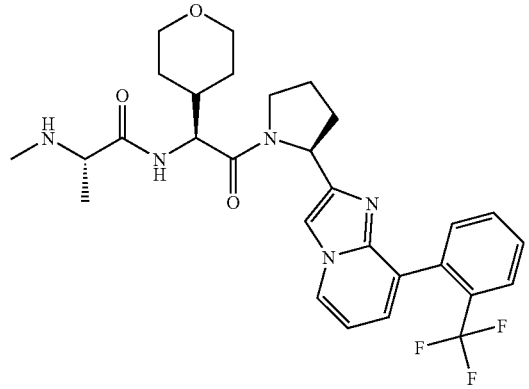

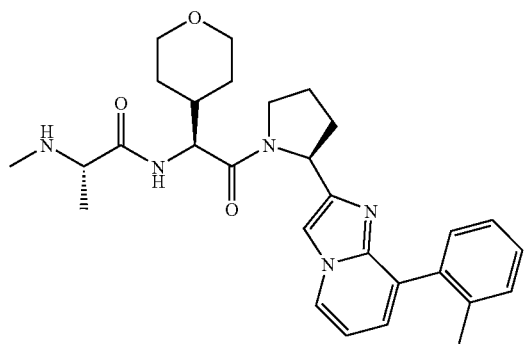

19

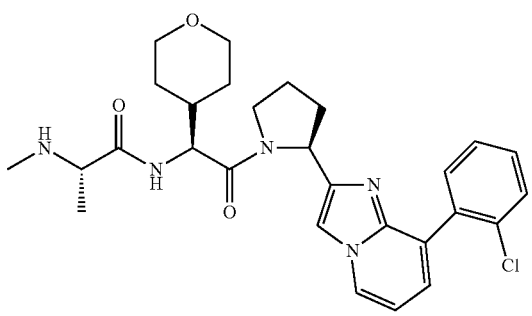

23

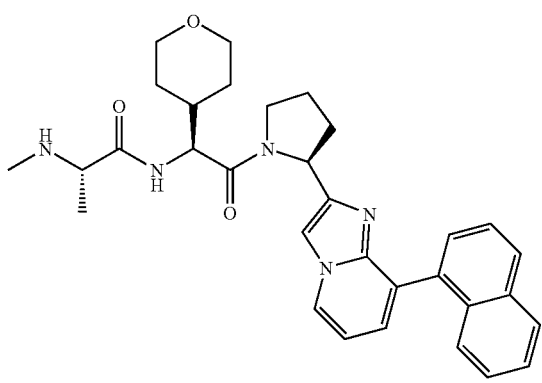

20

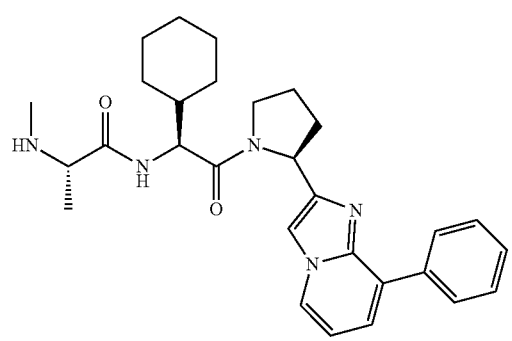

24

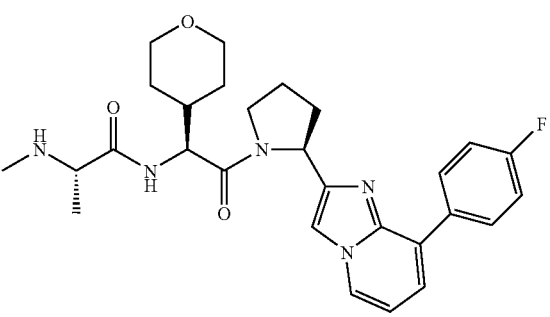

21

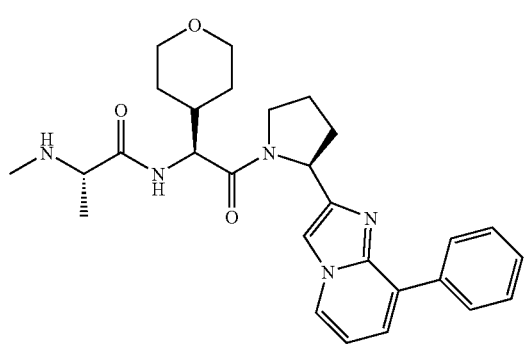

22

Compounds of the invention may exist in different resonance forms and that all such resonance forms are within the scope of the invention herein.

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection steps that are standard in organic synthesis may be required but may not be illustrated in the following general schemes. In a particular general synthetic scheme, compounds of the invention may be prepared by coupling amino acid residue analogues employing typical amide coupling procedures. In scheme 1, wherein Q, Y, Z, $R_1$, $R_6$ and $R_6'$ are as defined herein and Pr is a suitable protecting group, amine-protected amino acid residue analogues are coupled and deprotected sequentially to give the final compounds.

Scheme 1

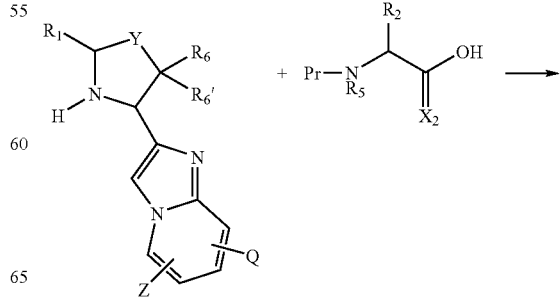

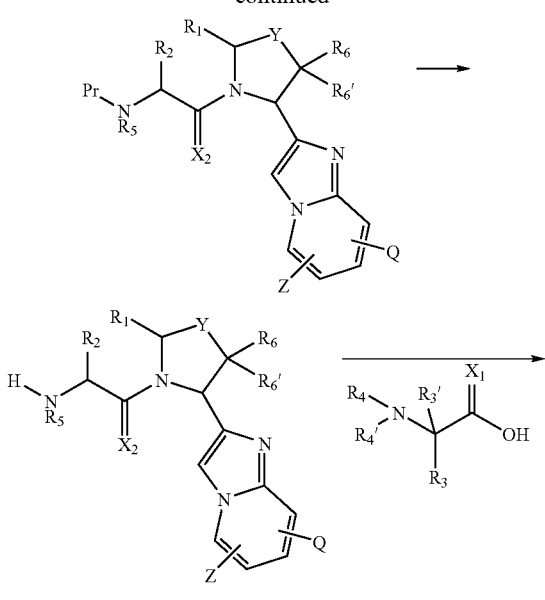

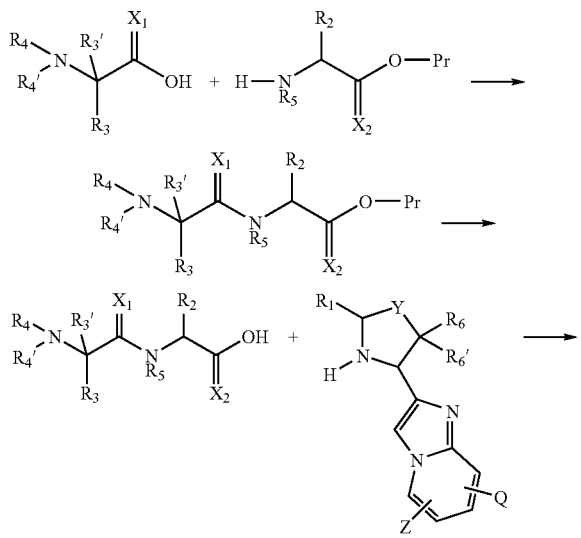

It will be appreciated that the amino acid analogs may be coupled in any order and may be prepared using solid phase support which is routine in the art. For example, Scheme 2 illustrates an alternative amino acid residue analogue coupling route.

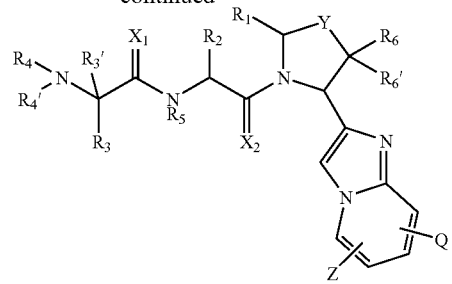

Imidazo[1,2a]pyridine intermediates may be prepared according to scheme 3 wherein Q, Y, Z, $R_1$, $R_6$ and $R_6'$ are as defined herein. Starting bromine a is reacted with 2-aminopyridyl b to give protected compound c which is subsequently deprotected to give intermediate d employed in synthesis of compounds of the invention.

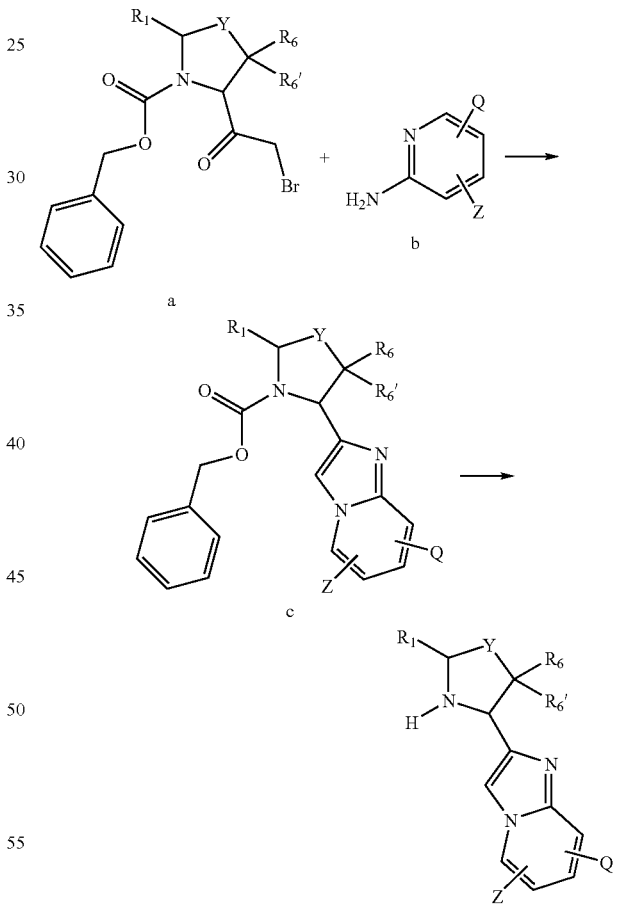

Compounds of the invention in which $R_4$ or $R_4'$ are other than H may be prepared according to standard organic chemistry techniques, for example by reductive amination in which a starting amino acid residue analog e.g. $NH_2$—$CH(R_3)$—$C(O)$—$OH$ is reacted with a suitable aldehyde or ketone to give the desired $R_4$ and $R_4'$ substituents. See scheme 4. The resulting $R_4/R_4'$ substituted amino acid intermediate can then be conjugated to the next amino acid intermediate or the remainder of the compound using standard peptide coupling procedures.

Scheme 4

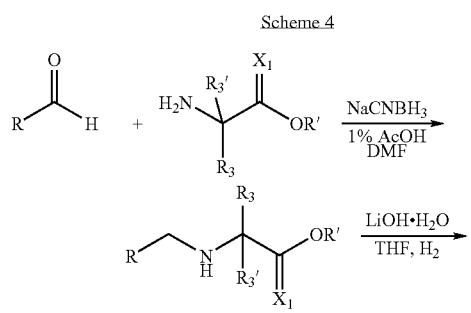

In a particular embodiment, alanine is reacted with 1-methylindole-2-carboxaldehyde and reduced with sodium cyanoborohydride dissolved in 1% HOAc/DMF to give the N-substituted alanine residue which may be used in preparing compounds of the invention. See scheme 5.

Scheme 5

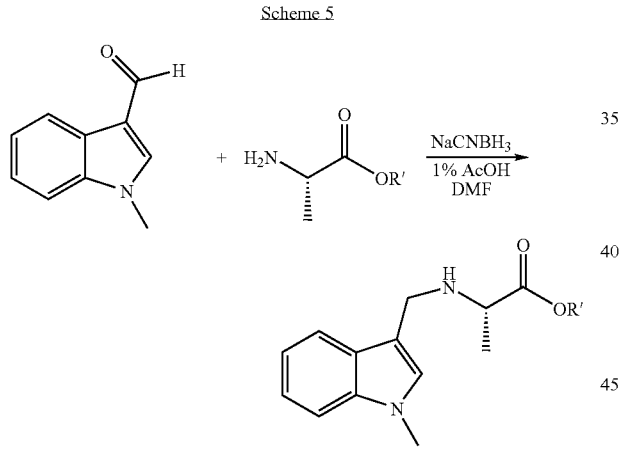

Alternatively, the reductive amination procedure to introduce $R_4/R_4'$ substituents is the final step in the preparation of the compound.

When compounds of the invention incorporate $R_4$ or $R_4'$ substituents other than H, they may also be prepared by substitution of a suitable acid intermediate which incorporates a leaving group with a desired amine. For example Br—CH($R_3$)—C(O)—OH is substituted with an amine $R_4$—$NH_2$ or $R_4$—NH—$R_4'$ according to scheme 6.

Scheme 6

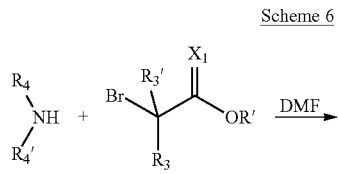

-continued

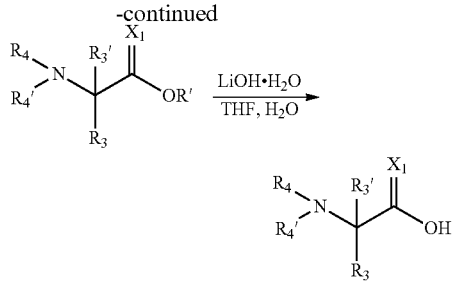

Alternatively, the substitution reaction introducing $R_4$ or $R_4'$ substituents may be performed as a final step in the preparation of the compound as illustrated in scheme 7.

Scheme 7

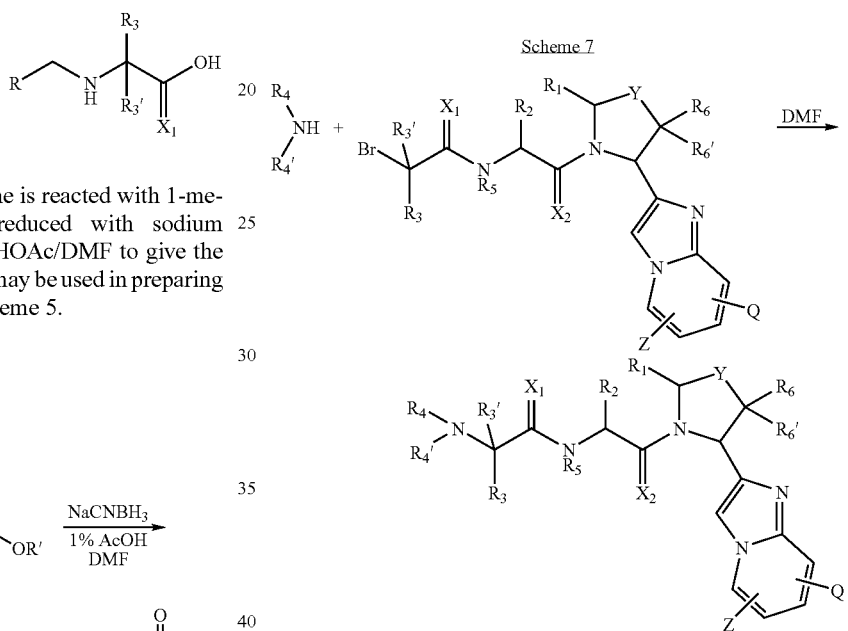

In a particular embodiment, the following amines used in schemes 6 and 7:

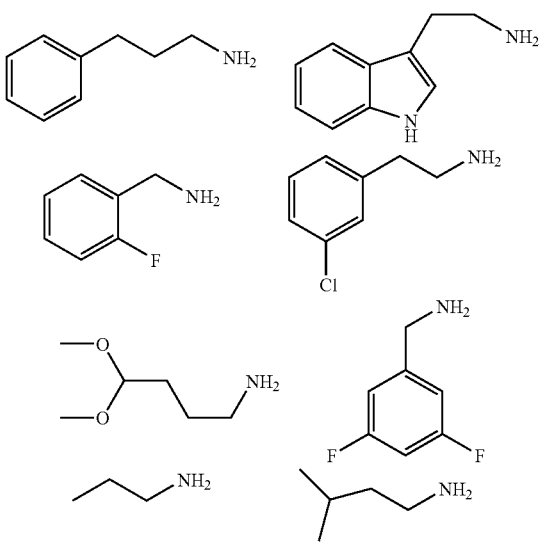

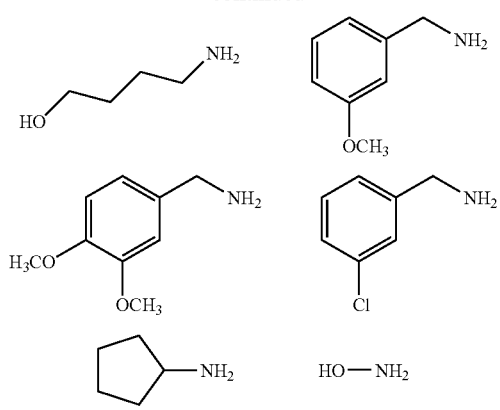

Compounds of the invention in which either $X_1$ or $X_2$ is sulfur, i.e. the compound incorporates a thioamide, may be prepared according to established organic chemistry techniques. For example, compounds in which $X_2$ is sulfur can be prepared according to scheme 8 starting from an Fmoc protected amino acid residue analog $NH_2$—$CH(R_2)$—$COOH$ which is dissolved in THF and cooled to −25° C., with addition of DIPEA followed by addition of isobutylchloroformate. After 10 minutes, the diamine, 4-nitrobenzene-1,2-diamine, is added and the reaction mixture is continuously stirred at −25° C. for 2 hours, then at room temperature overnight. THF is vacuumed off and the mixture is then subjected to flash chromatography using 50% EtOAc/Hexane to yield the product. The Fmoc-alanine derivative, phosphorus pentasulfide and sodium carbonate are mixed in THF and stirred overnight. The solution is concentrated and direct chromatography using 80% EtOAc/Hexane yields the activated thioalanine. The activated thioalanine and sodium nitrite are then mixed in acetic acid and diluted with $H_2O$. The resulting precipitant is filtered and dried to yield the product. The thioalanine is coupled to an A ring substituted proline amino acid residue analog by dissolving both in DMF. The thioamide product may then be deprotected with 20% PIP/DMA for 15 minutes and used to conjugate to the $R_4/R_4'$—N—$C(R_3)(R_3')$—COOH. Alternatively the Fmoc-protected thioamide is first coupled to the A ring substituted proline amino acid residue analog followed by Fmoc deprotection and subsequent coupling to the $R_4/R_4'$—$R_4/R_4'$—N—$C(R_3)(R_3')$—COOH amino acid residue analog.

Scheme 8

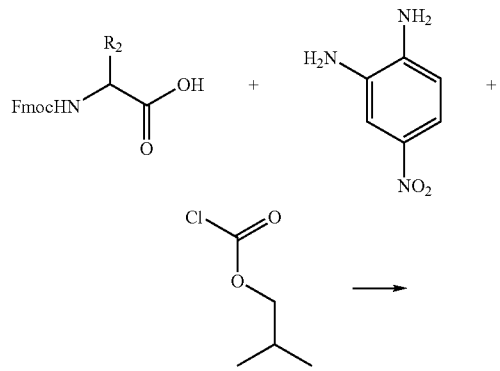

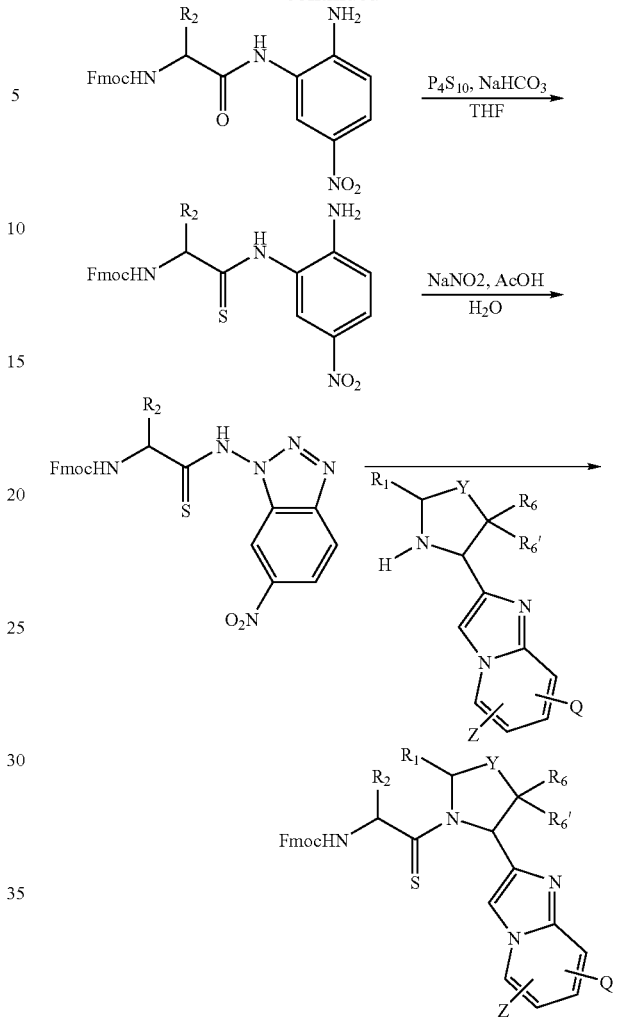

Indications

The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins. Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C. In a particular embodiment, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In an embodiment, the death receptor ligand is TNF-α. In a particular embodiment, the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. In an embodiment, the inhibitory compound for use herein is sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is may be below the amount that is toxic to normal cells, or the mammal as a whole.

Generally, the initial pharmaceutically effective amount of the compound of the invention administered parenterally per dose will be in the range of about 0.01-100 mg/kg, for example about 0.1 to 20 mg/kg of patient body weight per day, with the typical initial range of compound used being 0.3 to 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Reagents and solvents were obtained from commercial sources and used as received. Unjless otherwise noted, chromatographic purifications were performed using pre-packed silica gel columns on a CombiFlash Companion system by Teledyne-Isco, Inc. Lincoln, Nebr. The identity and purity of compounds were checked by LCMS and $^1$H NMR analysis.

Abbreviations used herein are as follows:
AcOH: acetic acid;
ACN: acetonitrile;
Chg: cyclohexylglycine;
DCM: dichloromethane
DIPEA: diisopropylethylamine;
DMAP: 4-dimethylaminopyridine;
DME: 1,2-dimethoxyethane;
DMF: dimethylformamide;
DMSO: dimethylsulfoxide
EDC: 1-ethyl-3-(3-dimethylaminopropyl)carbodiimide;
EEDQ: 2-ethoxy-1-ethoxycarbonyl-1,2-dihydroquinoline;
EtOAc: ethylacetate
EtOH: ethanol;
LCMS: liquid chromatography mass spectrometry;

HATU: O-(7-Azobenzotriazol-1-yl)-1,1,3,3-tetramethyluronium hexafluorophosphate;
HOBt: N-Hydroxybenzotriazole
HBTU: 2-(1H-Benzotriazol-1-yl)-1,1,3,3-Tetramethyl-uronium Hexafluorophosphate;
HPLC: high performance liquid chromatography;
MeOH: methanol;
NBS: N-bromosuccinamide;
TASF: tris(dimethylamino)sulfonium difluorotrimethylsilicate;
TEA: triethylamine;
TFA: trifluoroacetic acid;
THF: tetrahydrofuran;

Example 1

2-[tert-Butoxycarbonyl-(1H-pyrrol-2-ylmethyl)-amino]-propionic acid

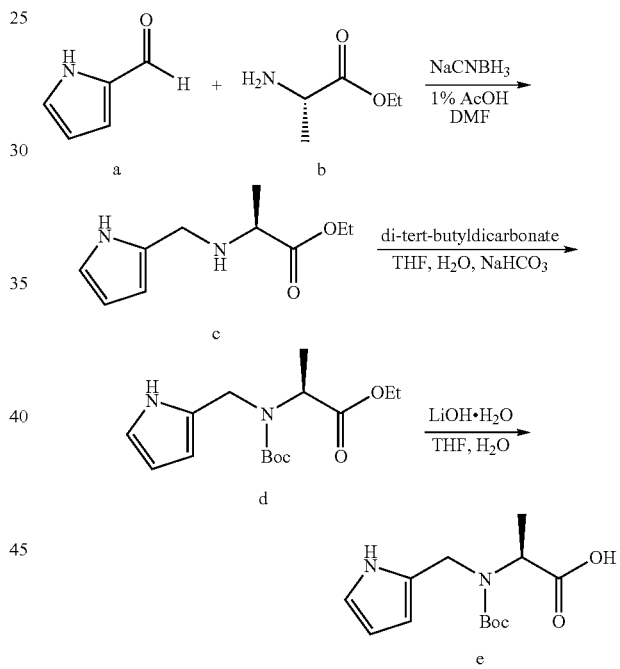

Alanine ethyl ester b (5 g, 32.5 mmol), pyrrole-2-carboxaldehyde a (3.1 g, 32.5 mmol), sodium cyanoborohydride (2.04 g, 32.5 mmol) and AcOH (1%) were mixed in DMF and stirred overnight. The reaction was quenched with $H_2O$, and DMF was evaporated. The mixture was diluted with EtOAc, washed by 0.1N NaOH, dried and concentrated to yield product c 2.5 g. The resulting ester c (2.5 g, 12.8 mmol), di-tert-butyldicarbonate (3.06 g, 14 mmol) were mixed in THF, $H_2O$ with NaHCO$_3$ and stirred overnight. THF was evaporated, and the mixture was diluted with EtOAc, washed by 1N NaOH, sat. NH$_4$Cl and brine. After dried, the mixture was concentrated to yield the Boc-protected ester d 3.3 g. The Boc-protected ester d (1.67 g, 5.6 mol), lithium hydroxide mono hydrate (284 mg, 6.77 mmol) were mixed in THF and $H_2O$ at 0° C. THF was vacuumed off, and the solution was acidified by dilute $H_2SO_4$, extracted by EtOAc twice. Organic layers were combined, dried and evaporated giving product 2-[tert-butoxycarbonyl-(1H-pyrrol-2-ylmethyl)-amino]-propionic acid e.

Example 2

Tetrahydropyranylglycine

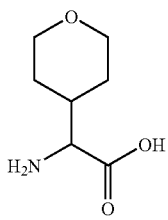

Tetrahydropyranylglycine was purchased from NovaBiochem, or synthesized according to the literature: Ghosh, A. K.; Thompson, W. J.; holloway, M. K.; McKee, S. P.; Duong, T. T.; Lee, H. Y.; Munson, P. M.; Smith, A. M.; Wai, J. M; Darke, P. L.; Zugay, J. A.; Emini, E. A.; Schleife, W. A.; Huff, J. R.; Anderson, P. S. *J. Med. Chem.*, 1993, 36, 2300-2310.

Example 3

Piperidinylglycine

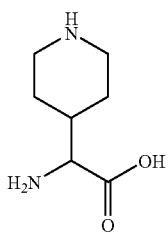

Piperidinylglycine was synthesized according to the procedures described by Shieh et al. (*Tetrahedron: Asymmetry*, 2001, 12, 2421-2425).

Example 4

4,4-difluorocyclohexylglycine

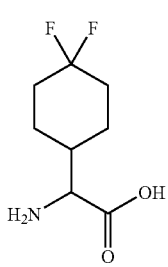

4,4-difluorocyclohexylglycine was made according to the procedures described in patent application US 20030216325.

Example 5

Boc (S)-2-amino-2-(4-hydroxycyclohexyl)acetic acid

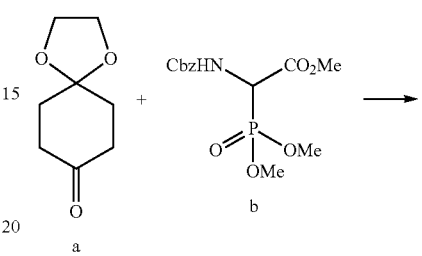

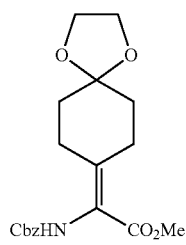

Following the procedure described by Sheih et al. (*Tetrahedron: Asymmetry*, 2001, 12, 2421-2425), a solution of ketone a (8.4 g) and EtOAc (30 mL) was added to a solution of N-Cbz-phosphonoglycine methyl ester b, TMG (4.5 mL) and EtOAc (30 mL). The solution was maintained at rt for 48 h, then washed with 1N HCl (3×50 mL), brine (1×50 mL) dried ($Na_2SO_4$), filtered, and concentrated. The residue was adsorbed onto Celite, and purified by chromatography, then further purified by re-crystallization from EtOAc/hexanes to afford 5.2 g of product c.

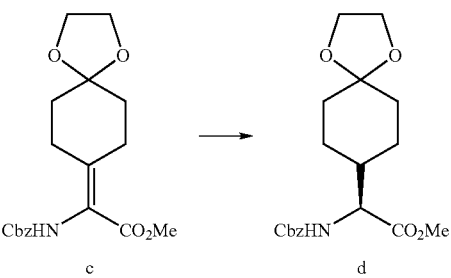

Following the procedure described by Sheih, (*Tetrahedron: Asymmetry*, 2001, 12, 2421-2425), a solution of eneamide c (5.0 g), (S,S)-Me-BPE-Rh(I) (1.5 g, Strem Chemicals, Newburyport, Mass.), and MeOH (100 mL) was shaken vigorously under 70 psi of $H_2$ for 48 h. The solvent was removed under reduced pressure. The residue was taken up in EtOAc, and filtered through $SiO_2$ with more EtOAc. The solvent was removed under reduced pressure to afford 4.0 g of product d as a colorless solid.

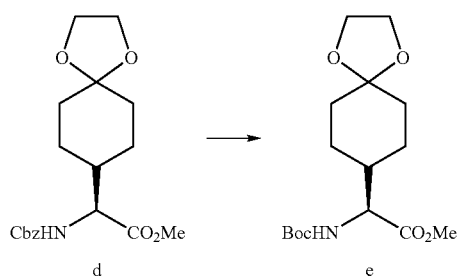

A mixture of Cbz-carbamate d, (4.0 g) Boc₂O, (2.9 g), 20% Pd(OH)₂.C (1.0 g) and MeOH (30 mL) was maintained under an atmosphear of H₂ for 6 h. The mixture was filtered through Celite with MeOH. The solvent was removed under reduced pressure to afford 4.5 g of residue e, which was taken on directly.

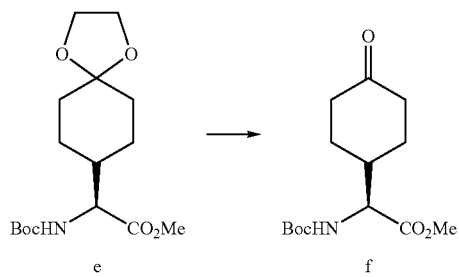

The residue e from above was dissolved in H₂O (10 mL), AcOH (30 mL), THF (5 mL), and dichloroacetic acid (3 mL) and maintained at rt overnight. Water (5 mL) was added and the solution and maintaned until hyrolysis was complete, as monitored by HPLC-MS. Solid Na₂CO₃ was added cautiously until gas evolution ceased, the mixture was diluted with aq NaHCO₃, and extracted with 10% EtOAc/DCM. The combined organic phases were washed once with brine, dried (Na₂SO₄), filtered, and concentrated. The residue was purified by chromatography to afford 2.9 g of product f.

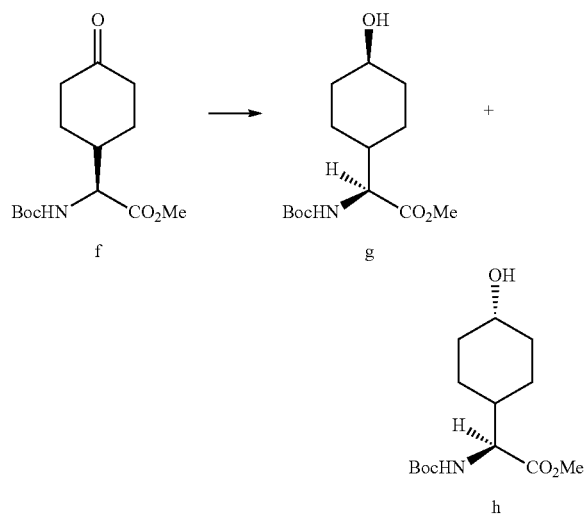

A mixture of ketone f (1.5 g) MeOH (50 ml) was treated with NaBH4 (290 mg) at 0° C. for 20 min. The mixture was acidifed to ~pH1 with 10% aq citric acid and the MeOH was removed under reduced pressure. The residue was diluted with water and extraced with 20% EtOAc/DCM. The combined organic phases were washed once with brine, dried (Na₂SO₄), filtered, and concentrated. The residue was purified by chromatography to afford 1.17 g of product g and 0.23 g of product h.

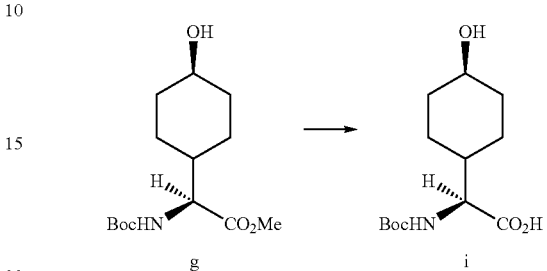

A mixture of ester g (1.17 g) LiOH.H2O (160 mg), THF (3 mL) and water (4.5 mL) was stirred vigorously at rt overnight. The mixture was diluted with brine and exaustivly extraced with EtOAc. The combined organic phases were washed once with brine, dried (Na₂SO₄), filtered, and concentrated to afford acid i (525 mg).

Example 6

N-Boc-N-cyclopropylmethyl-L-alanine

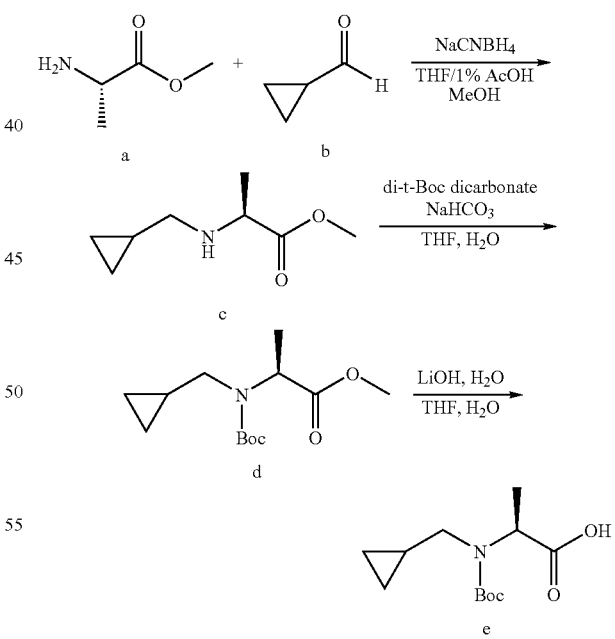

L-alanine methyl ester hydrochloride a (5 g, 35.8 mmol) and cyclopropanecarboxaldehyde b (2.67 ml, 35.8 mmol) were suspended in 50 ml THF w/1% AcOH. Addition of 5 ml of CH₃OH made the cloudy solution turned to clear. NaC-NBH₄ (2.25 g, 35.8 mmol) was added and the reaction mixture stirred overnight. The reaction was quenched by addition of 1N aq. NaOH, extracted by EtOAc twice, organic layers were dried over Na$_2$SO$_4$ and concentrated to dryness. The crude material was purified by chromatography using 30% EtOAc/hexane (stained by ninhydrin) to obtain the compound c (1 g, 18%). The compound c (1 g, 6.37 mmol) and di-t-bocdicarbonate (2.1 g, 9.55 mmol) were diluted in THF (20 ml) and H$_2$O (20 ml), NaHCO$_3$ (1.3 g, 15.9 mmol) was added. The reaction mixture stirred overnight for completion. THF was removed under reduced pressure, and the aqueous layer was extracted by EtOAc 3 times. Combined organic layers were washed by 1N NaOH, sat, NH$_4$Cl followed by brine, the concentrated to dryness. The Boc-protected compound d (1.39 g, 5.40 mmol) was stirred with LiOH.H$_2$O (1.14 g, 27 mmol) in THF (20 ml) and H$_2$O (20 ml) overnight at room temperature. THF was stripped off, and the aqueous layer was adjusted to pH=4 by adding 10% citric acid, then extracted by EtOAc 3 times. Combined organic layers were washed by brine and concentrated. The crude was purified by reverse phase C-18 column eluted by 0%-50% acetonitrile/H$_2$O to give pure compound e as a white solid (794 mg).

Example 7

N-Boc-N-methyl-L-alanine-L-cyclohexylglycine

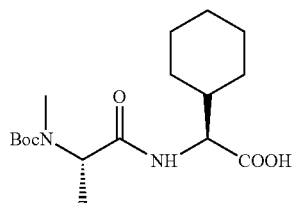

A solution of Fmoc-L-cyclohexylglycine (3.6 g, 9.6 mmol) dissolved in DCM (50 mL) and DIPEA (5.6 mL, 32 mmol) was added to 2-chlorotrityl chloride resin (5 g, 8 mmol) and gently agitated for 3 hours at room temperature. The resin was washed with DCM 4 times, DCM/MeOH/DIPEA (17:2:1) 3 times, DCM 3 times, and 2 times dimethylacetamide (DMA). The Fmoc group was removed by treating the resin with 20% piperidine/DMA (50 mL) for 15 minutes. The resin was washed with DMA 6 times. A solution of Boc-N-methylalanine (3.3 g, 16 mmol), HBTU (6.1 g, 16 mmol), and DIPEA (5.6 mL, 32 mmol) and DMA/DCM (1:1, 50 mL) was added to the resin and gently agitated for 2 hours at room temperature. The resin was washed with DMA 5 times, DCM 2 times, and dried under reduced pressure. The dipeptide was cleaved from the resin by gentle agitation with HOAc/TFE/DCM (1:1:3, 100 mL) for 2 hours at room temperature. The resin was removed by filtration and the solution concentrated. Residual AcOH was removed by azeotroping with hexanes (15 times volume). The solid residue was purified by reverse-phase HPLC (C$_{18}$, MeCN—H$_2$O, 0.1% TFA) and the solvents removed by lyophylization to provide 1.2 g (43%) of dipeptide N-Boc-N-methyl-L-alanine-L-cyclohexylglycine as a white powder.

Example 8

N-Boc-N-methyl-L-alanine-L-dehydropyranylglycine

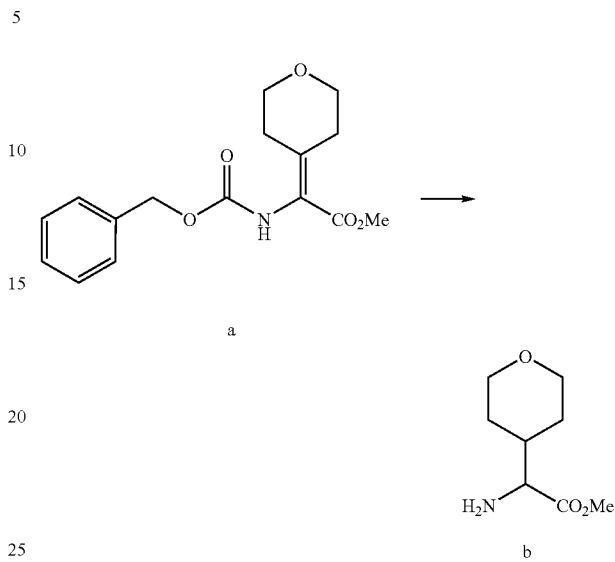

A mixture of N-Cbz-dehydropyranylglycine methyl ester a (Burk, M. J.; Gross, M. F.; Martinez, J. P. *J. Am. Chem. Soc.* 1995, 117, 9375, and references therein) (5.2 g, 17 mmol), 5% Pd.C (500 mg), MeOH (75 mL) and THF (25 mL) was maintained under an atmosphere of H$_2$ for 24 h. The mixture was filtered through Celite and the Celite washed with MeOH, and concentrated under reduced pressure to afford a quantitative yield of amine b as a colorless oil, which was carried on directly.

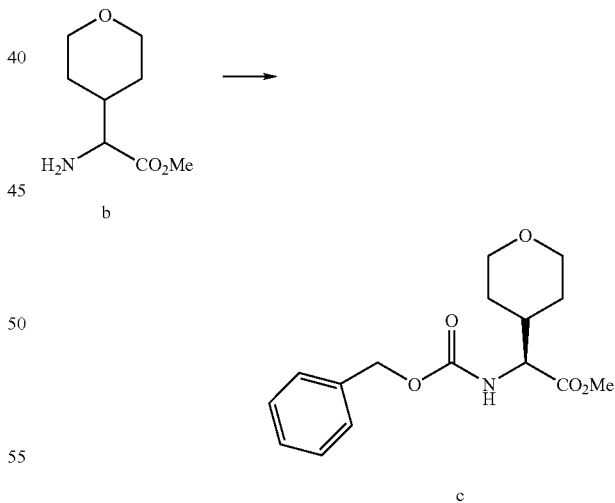

The amine b prepared above was combined with CH$_2$Cl$_2$ (40 mL), saturated aqueous NaHCO$_3$ (40 mL) and cooled to 0° C. Benzyloxy carbonyl chloride (3.0 mL) was then added dropwise and the mixture stirred vigorously overnight. The phases were separated and the aqueous phase extracted with CH$_2$Cl$_2$ (3×20 mL). The combined organic phases were washed with brine (1×50 mL), dried (Na$_2$SO$_4$), filtered, adsorbed onto Celite and chromatographed (ISCO, 120 g silica column, gradient elution 5-55% EtOAc-hexanes) to afford 4.15 g (80%) of racemic Cbz-pyranylglycine methyl ester. The enantiomers were separated on a Chiracel OD column eluting with 10% EtOH-hexanes. The desired S-enantiomer c elutes first under these conditions.

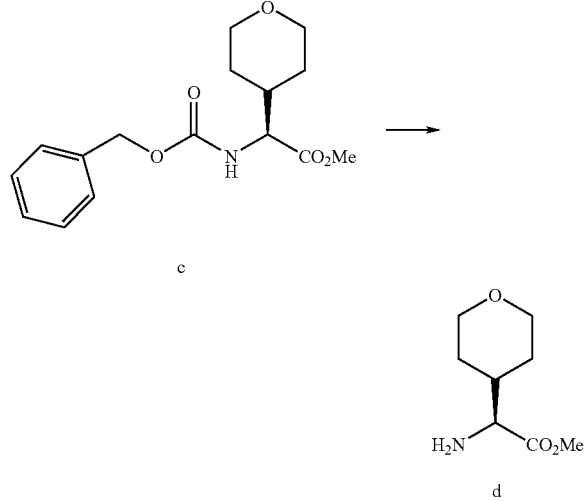

A mixture of (S)—N-Cbz-pyranyl glycine c methyl ester (2.4 g, 7.82 mmol) 10% Pd.C (700 mg), MeOH (80 mL) was maintained under 1 atmosphere of $H_2$ for 24 h. The mixture was filtered through Celite with MeOH, and concentrated under reduced pressure to afford 1.35 g (100%) of amine d as a colorless oil. Alternatively, pyranyl glycine can be synthesized in enantiopure form following the procedure of Ghosh (Ghosh, A. K.; Thompson, W. J.; Holloway, M. K.; McKee, S. P.; Duong, T. T.; Lee, H. Y.; Munson, P. M.; Smith, A. M.; Wai, J. M.; Darke, P. L.; Zugay, J. A.; Imini, E. A.; Schleif, W. A.; Huff, J. R.; Anderson, P. S. *J. Med. Chem.*, 1993, 36, 2300).

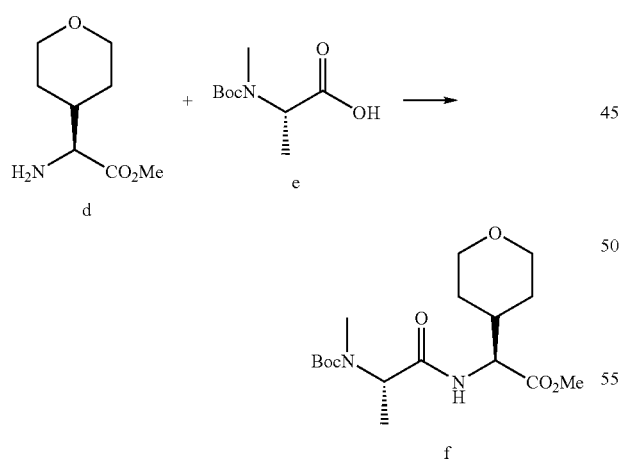

A mixture of amine d (1.35 g, 7.8 mmol), N-Boc-N-methyl alanine e (1.74 g, 8.6 mmol), EDC (1.65 g 8.8 mmol) and MeCN (50 mL) was maintained at rt overnight. The MeCN was removed under reduced pressure, and the residue diluted with EtOAc, washed with 0.5 N HCl (3×10 mL), 0.5 N NaOH (3×10 mL), dried ($MgSO_4$), filtered, and concentrated to provide 2.1 g (75%) of protected dipeptide f, as a clear oil.

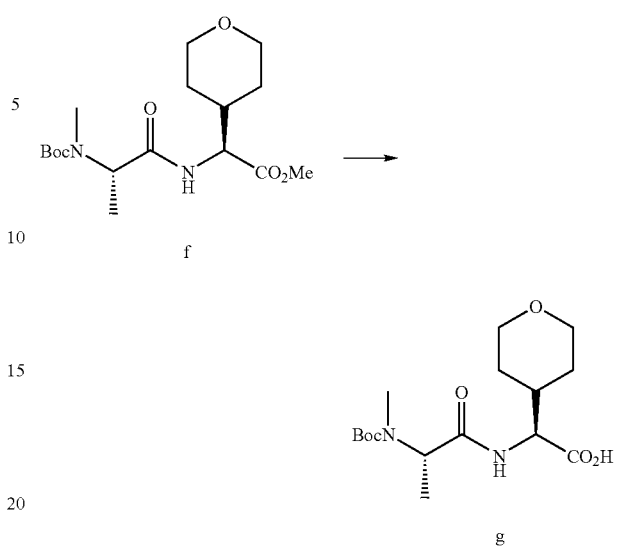

To a 0° C. solution of ester f (2.10 g, 5.86 mmol) and THF (50 mL) were added $LiOH.H_2O$ (1.23 g, 29.3 mmol) and water (2 mL). The mixture was maintained at 0° C. for 2 h, then the cooling bath was removed and the mixture was stirred overnight. Most of the THF was then removed under reduced pressure and the residue was diluted with $CH_2Cl_2$, washed with 0.5 N HCl, dried ($MgSO_4$), filtered, and concentrated to provide 1.53 g (78%) of dipeptide N-Boc-N-methyl-L-alanine-L-dehydropyranylglycine g, as a colorless solid.

Example 9

N-Boc-protected Cyclic Sulfonyl Amino Acid

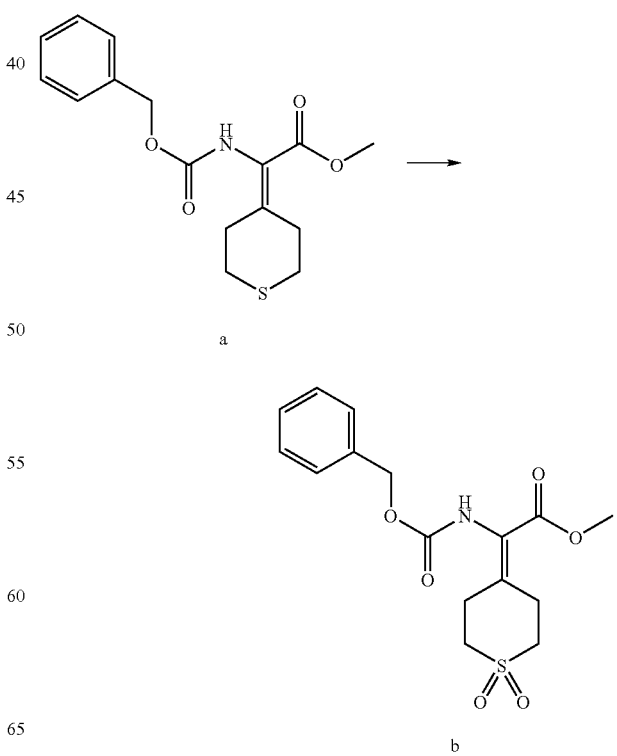

Sulfide a (810 mg, 2.5 mmol), synthesized according to the general procedure of Shieh [Shieh, W-C.; Xue, S.; Reel, N.; Wu, R.; Fitt, J.; Repic, O. *Tetrahedron: Asymmetry*, 2001, 12, 2421-2425], was dissolved in methanol (25 mL). Oxone (4.5 g) was dissolved in deionized water (25 mL). The methanol solution of substrate was cooled to −10° C., and the aqueous solution of oxone was added to the reaction slowly. The reaction was kept on ice and gradually allowed to warm to room temperature while stirring overnight. Deionized water was used to dilute the reaction to approximately 150 mL, then poured into 90% ethyl acetate-hexanes for extraction. The organic phase was dried ($Na_2SO_4$), adsorbed onto Celite and purified by chromatography ISCO CombiFlash 40 g column, 5-90% ethyl acetate-hexanes over 30 min to afford 804 mg (2.27 mmol, 91%) of the product sulfone b.

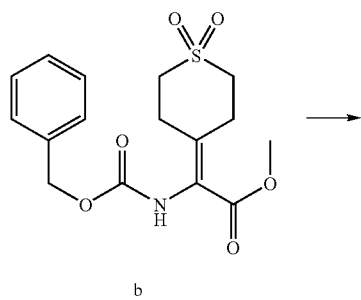

b

Following the general procedure of Burk [Burk, M. J.; Gross, M. F.; Martinez, J. P. *J. Am. Chem. Soc.* 1995, 117, 9375-9376.], alkene b (774 mg 2.19 mmol), dry methanol (40 mL), and [(S,S)-Me-BPE-Rh(COD)]$^+$OTf$^-$ (500 mg, 0.8 mmol) were mixed in a Parr shaker flask purged with nitrogen. The Parr flask was evacuated and subsequently charged to 60 psi with hydrogen gas and shaken vigorously overnight. Methanol was removed under reduced pressure, and crude product was filtered through a small plug of silica gel using ethyl acetate. Evaporation of the solvent yielded 730 mg (2.0 mmol, 94%) of product c with >98% yield.

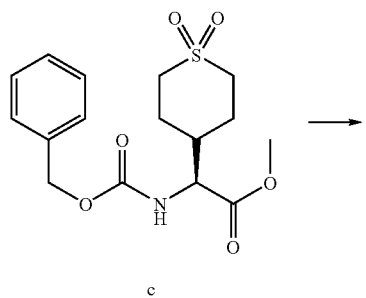

c

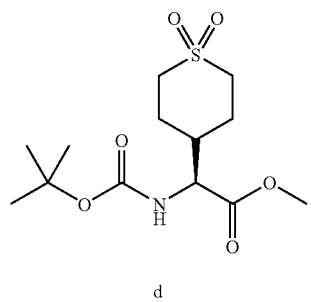

d

Z-protected amino ester c (804 mg, 2.27 mmol) was dissolved in methanol (16 mL). To this solution was added BOC-anhydride (1.5 g, 6.8 mmol), followed by 20% Pd(OH)$_2$.C (250 mg). All air was removed from the reaction flask by house vacuum, and the mixture was stirred vigorously for 5 min. The flask was then filled with hydrogen gas and allowed to stir vigorously at room temperature for 6 h. After evacuating the hydrogen atmosphere, the mixture was filtered through Celite using methanol, and crude product d was obtained by evaporation of the solvent (508 mg, 1.56 mmol, 70% yield).

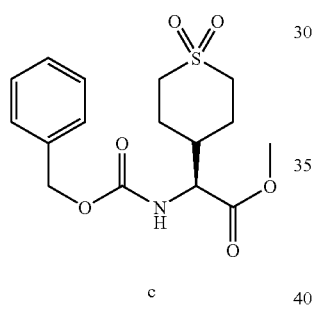

d

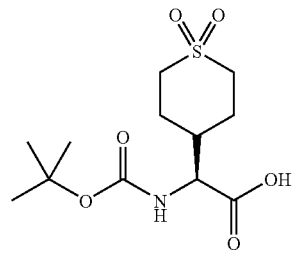

e

Ester d (508 mg, 1.56 mmol) was dissolved in 8 mL of THF. Deionized water (4 mL) was added, followed by LiOH.H$_2$O (120 mg, 2.8 mmol). The mixture was stirred at room temperature overnight, acidified using aqueous 1 N HCl and extracted into ethyl acetate (3×25 mL). The organic extracts were dried further with $Na_2SO_4$, filtered and concentrated to give 372 mg (1.21 mmol, 78% yield) of the N-Boc-protected cyclic sulfonyl amino acid e, which was carried on without purification.

Example 10

N-Boc-N-methyl-L-glycine

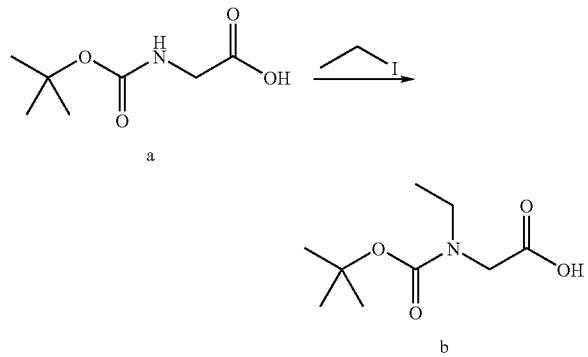

Following the general procedure of Grigg [Blaney, P.; Grigg, R.; Rankovic, Z.; Thornton-Pett, M.; Xu, J. *Tetrahedron*, 2002, 58, 1719-1737] a roundbottom flask was charged with sodium hydride (480 mg 60% dispersion in oil, 12.0 mmol, 4.0 equiv) and purged with nitrogen for 15 min. THF (6.0 mL) was added to the flask, and the suspension was cooled to 0° C. using an ice water bath. A separate flask was charged with BOC-glycine a (525 mg, 3.0 mmol), dry THF (6.0 mL) and ethyl iodide (1.0 mL, 12 mmol, 4 equiv). This mixture was added dropwise to the NaH suspension in THF, with vigorous stirring at 0° C. After 1 h of stirring, the reaction was warmed to room temperature and allowed to stir overnight. The reaction was again cooled to 0° C., and methanol (4 mL) was added very slowly to quench the excess hydride. Deionized water was added to dilute the mixture, and methanol was removed under reduced pressure. Impurities were extracted into 90% ethyl acetate-hexanes, the aqueous layer was then acidified by adding solid citric acid until the pH reached 2-3. The product was extracted into 90% ethyl acetate-hexanes. This organic layer was dried (Na$_2$SO$_4$) and filtered. Removal of the solvents under reduced pressure afforded a quantitative yield of the product b.

Example 11

N-Boc-fluoro-L-alanine

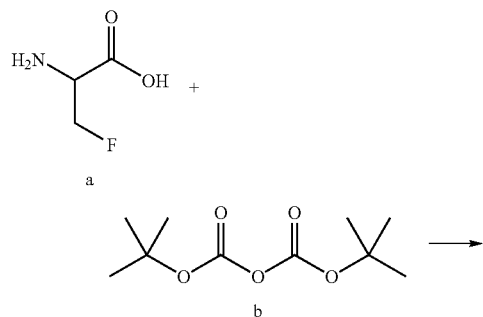

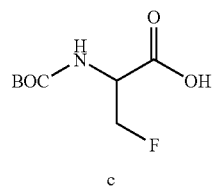

A mixture of unprotected amino acid a (775 mg, 7.24 mmol) and sodium carbonate (1.69 g, 16.0 mmol) was dissolved in a 1:1 solution of deionized water and THF (15 mL each). To this mixture was added BOC-anhydride b (1.73 g, 7.96 mmol). The mixture was stirred at room temperature overnight, and THF was removed under reduced pressure. The mixture was then acidified to pH 2-3 with saturated aqueous citric acid, and product was extracted into 10% ethyl acetate-dichloromethane. The organic layer was dried (Na$_2$SO$_4$), filtered and concentrated under reduced pressure to afford clean BOC-protected amino acid c (1.40 g, 6.7 mmol, 93%) to be used without further purification.

Example 12

Compound 1

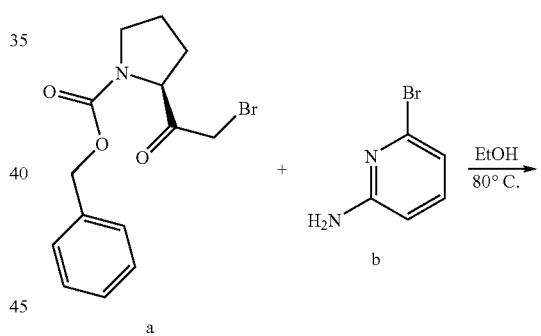

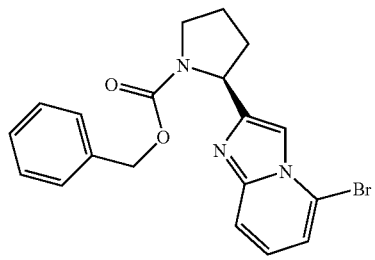

In a 100 mL round-bottomed flask, compound a (1.62 g, 4.97 mmol) and 2-amino-5-bromopyridine b (1.0 g, 6.00 mmol) were mixed together in ethanol (50 mL) and stirred at 80° C. for 48 h. The mixture was then cooled down and concentrated. The residue was adsorbed on silica gel and purified by flash chromatography (100% DCM to 10% Methanol/DCM) to afford 881 mg (35.4%) of compound c as an orange oil. LCMS: M/Z=401.

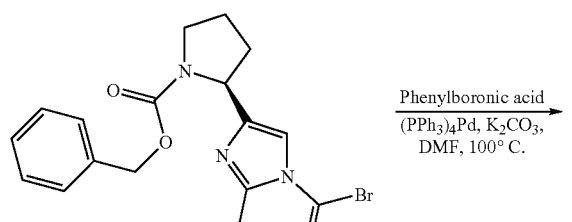

c

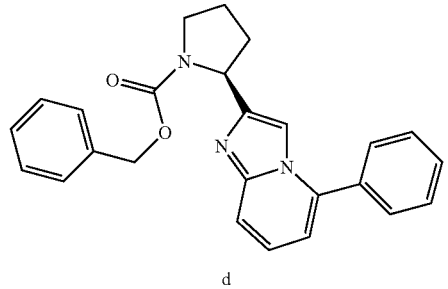

d

Into a 25 mL round-bottomed flask, compound c (150 mg, 0.37 mmol), phenylboronic acid (68 mg, 0.56 mmol), tetrakis(triphenylphosphine)palladium(0) (30 mg, 0.03 mmol) and potassium carbonate (78 mg, 0.56 mmol) were mixed together in DMF (2.0 mL). The mixture was stirred at 100° C. under nitrogen atmosphere for 18 h. The mixture was then cooled down, diluted with ethyl acetate (30 mL) and washed with water (50 mL). The aqueous phase was extracted with ethyl acetate (30 mL). The combined organic phases were washed with saturated aqueous NaHCO$_3$ (50 mL) and brine (50 mL), dried with MgSO$_4$, filtered and concentrated. The residue was adsorbed on silica gel and purified by flash chromatography (30% ethyl acetate/hexane to 100% ethyl acetate) to afford 126 mg (84%) of compound d as a pale yellow oil.
LCMS: M/Z=398.

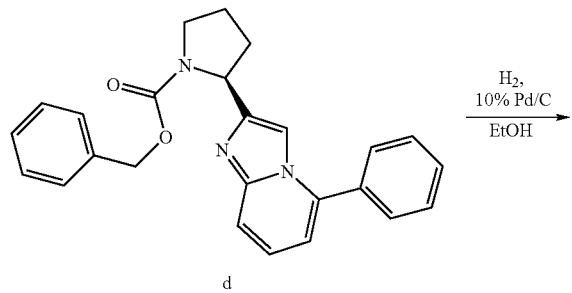

d

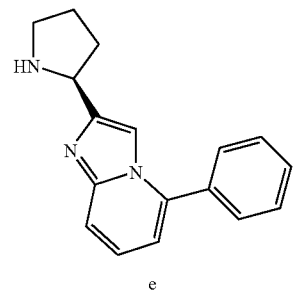

e

In a 50 mL round-bottomed flask, compound d (120 mg, 0.30 mmol) was dissolved in ethanol (10 mL) and 10% pal-ladium on carbon (24 mg) was added. The mixture was stirred at room temperature under a hydrogen atmosphere for 48 h. The mixture was then filtered over celite and washed with ethanol. The filtrate was concentrated to afford 78 mg (98%) of compound e as a pale yellow oil. LCSM: M/Z=264.

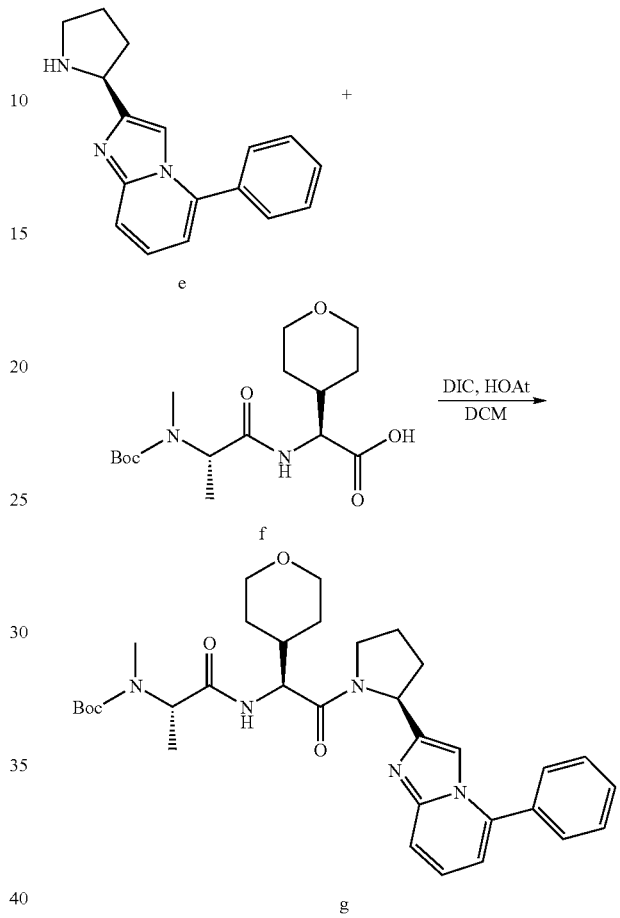

In a 10 mL round-bottomed flask, compound e (78 mg, 0.30 mmol), compound f (120 mg, 0.36 mmol), N,N-diisopropylcarbodiimide (0.074 mL, 0.47 mmol) and 1-hydroxy-7-azabenzotriazole (64 mg, 0.47 mmol) were mixed together in dichloromethane (2.0 mL). The mixture was stirred at room temperature under a nitrogen atmosphere for 5 h. The mixture was then concentrated on silica gel and purified by flash chromatography (100% DCM to 7% MeOH/DCM) to afford 182 mg (50%) of compound g as pale yellow oil. LCMS: M/Z=590.

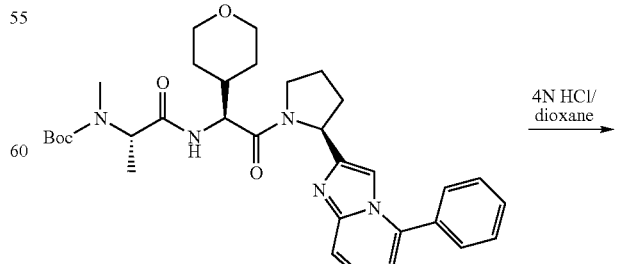

g

-continued

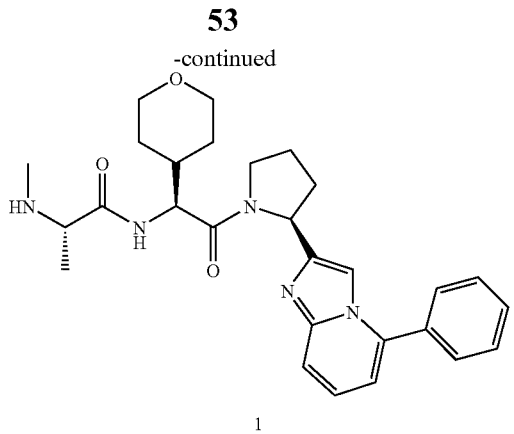

1

In a 25 mL round-bottomed flask, compound g (192 mg, 0.33 mmol) was dissolved in a solution of 4N hydrogen chloride in dioxane (4 mL, 30 mmol). The mixture was stirred at room temperature for 1 h. The mixture was then concentrated and the residue was purified by HPLC to afford 13.3 mg (8.3%) of compound 1 as a white solid. LCMS: M/Z=490.

Example 13

(S)-benzyl-2-(2-bromoacetyl)pyrrolidine-1-carboxylate

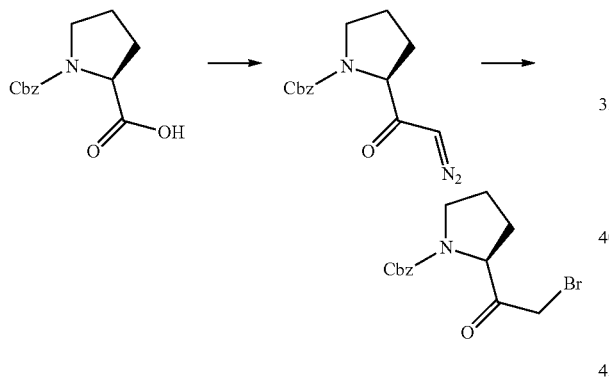

Alpha bromo ketone was prepared according to the general procedure of Bures and Kulhanek (*Tetrahedron: Assymetry* (2005) 16(7):1347-1354.)

A solution of Diazald (4.9991 g, 23.3 mmol), sodium sulfate (20.14 g), and diethyl ether (15 mL) was stirred for 15 min. The resulting mixture was then filtered and added dropwise to a solution of potassium hydroxide (5.0050 g) in water (8 mL) and ethanol (10 mL) at 65° C. in a mini Diazald apparatus and distilled until the reaction mixture was pale yellow. The distilled diazomethane solution was stored over sodium hydroxide pellets at 4° C.

To a solution of Cbz-Pro-OH (2.9986 g, 12.0 mmol) in dry tetrahydrofuran (40 mL) and dry diethyl ether (40 mL) was added triethylamine (1.7 mL, 12.2 mmol). The solution was cooled to −25° C. and isobutyl chloroformate (1.6 mL, 12.3 mmol) was added dropwise. The resulting solution was stirred at −25° C. for 30 min before warming to −10° C. The diazomethane solution was added to the reaction mixture. The sample was stirred at −10° C. for 1 hour. The reaction mixture was concentrated to one half of its original volume and washed once with saturated sodium bicarbonate (50 mL). The organic layer was dried over magnesium sulfate and filtered. The crude material was adsorbed onto silica gel and purified by flash chromatography (40 g SiO$_2$, 0-50% ethyl acetate in hexanes) to give the diazoketone (2.29 g, 8.3 mmol, 69%).

The diazoketone (1.72 g, 6.3 mmol) was dissolved in acetic acid (40 mL) and cooled to 0° C. 48% HBr (1.1 mL, 9.7 mmol) was added dropwise to the solution. The reaction mixture was warmed to room temperature and stirred for 1 hour. The sample was poured into ice and added sodium bicarbonate (5 g). The solution was extracted with dichloromethane (3×100 mL). The organic extracts were washed with saturated sodium bicarbonate (3×100 mL). The dichloromethane extracts were dried over magnesium sulfate, filtered, and concentrated to give the α-bromoketone (S)-benzyl-2-(2-bromoacetyl)pyrrolidine-1-carboxylate (1.771 g, 5.4 mmol, 86%). The α-bromoketone was unstable at room temperature as well as 4° C. when stored neat.

Example 14

(S)-benzyl 2-(8-phenylimidazo[1,2-a]pyridin-2-yl)pyrrolidine-1-carboxylate

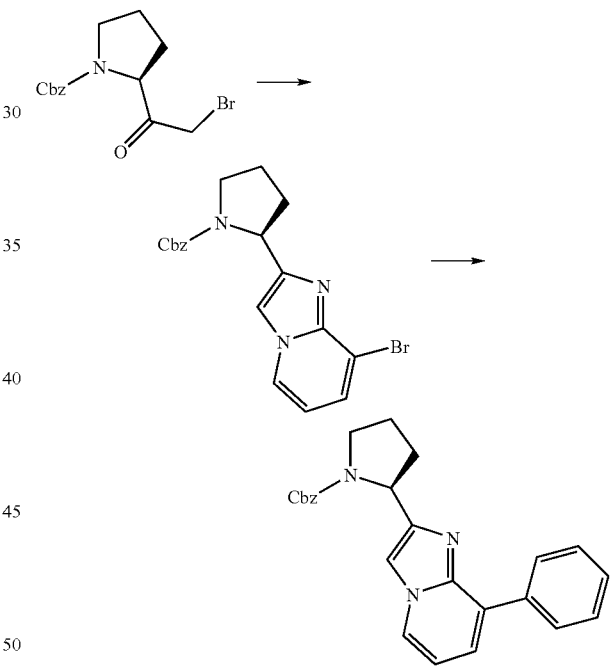

(S)-benzyl-2-(2-bromoacetyl)pyrrolidine-1-carboxylate (1.771 g, 5.4 mmol), 2-amino-3-bromo-pyridine (0.9412 g, 5.4 mmol), and ethanol (20 mL) were combined under nitrogen. The reaction mixture was heated to 78° C. and stirred overnight. The sample was concentrated and saturated sodium bicarbonate (50 mL) was added. The mixture was extracted with ethyl acetate (3×50 mL). The ethyl acetate extracts were dried over magnesium sulfate and filtered. The crude material was adsorbed onto silica gel and purified by flash chromatography (40 g SiO$_2$, 0-100% ethyl acetate in hexanes) to give (S)-benzyl-2-(8-bromoimidazo[1,2-a]pyridin-2-yl)pyrrolidine-1-carboxylate (0.869 g, 8.3 mmol, 2.2 mmol, 40%).

To a 2-5 ml microwave vial with a stirbar was added (S)-benzyl-2-(8-bromoimidazo[1,2-a]pyridin-2-yl)pyrrolidine- 1-carboxylate (0.258 g, 0.644 mmol), phenylboronic acid (0.1026 g, 0.8415 mmol) and potassium carbonate (0.142 g, 1.03 mmol). The reaction vial was evacuated and purged with $N_2$ three times. Tetrakis(triphenylphosphine)-palladium(0) (0.0395 g, 0.0342 mmol) was then added and the vial evacuated and purged with $N_2$ five times. 3 ml of DMF was added, then 1 ml of deoxygenated $H_2O$, and the vial was microwaved at 130° C. for 40 min. LC/MS showed no starting material remaining, so the reaction was poured into 200 ml $H_2O$ and extracted with ethyl acetate (3×50 ml) and the combined extracts were dried with $MgSO_4$, filtered and concentrated under reduced pressure. The crude material was dissolved in dichloromethane and applied to a 12 g column which had been equilibrated in hexanes. The material was flashed using a gradient of 0% to 50% ethyl acetate in hexanes. The product containing fractions were combined and evaporated under reduced pressure to give the desired imidazopyridine (S)-benzyl 2-(8-phenylimidazo[1,2-a]pyridin-2-yl)pyrrolidine-1-carboxylate.

Example 15

(2S)-benzyl 2-(8-o-tolylimidazo[1,2-a]pyridin-2-yl)pyrrolidine-1-carboxylate

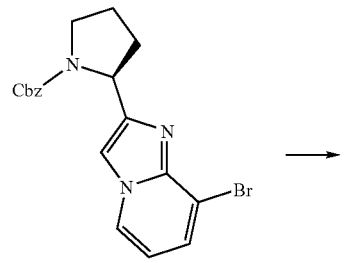

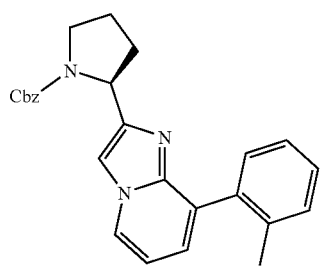

Following procedures of example 14, (S)-benzyl-2-(8-bromoimidazo[1,2-a]pyridin-2-yl)pyrrolidine-1-carboxylate (0.250 g, 0.62 mmol), o-tolyl boronic acid (0.1101 g, 0.81 mmol), potassium carbonate (0.1292 g, 0.93 mmol), and tetrakis(triphenylphosphine)palladium(0) (0.0360 g, 0.03 mmol) were reacted to give crude (2S)-benzyl 2-(8-o-tolylimidazo[1,2-a]pyridin-2-yl)pyrrolidine-1-carboxylate. The crude material was adsorbed onto silica gel and purified by flash chromatography (4 g $SiO_2$, 0-70% ethyl acetate in hexanes) to give the final product (0.247 g, 0.60 mmol, 74%).

Example 16

(2S)-benzyl-2-(8-(2-(trifluoromethyl)phenyl)imidazo[1,2-a]pyridin-2-yl)pyrrolidine-1-carboxylate

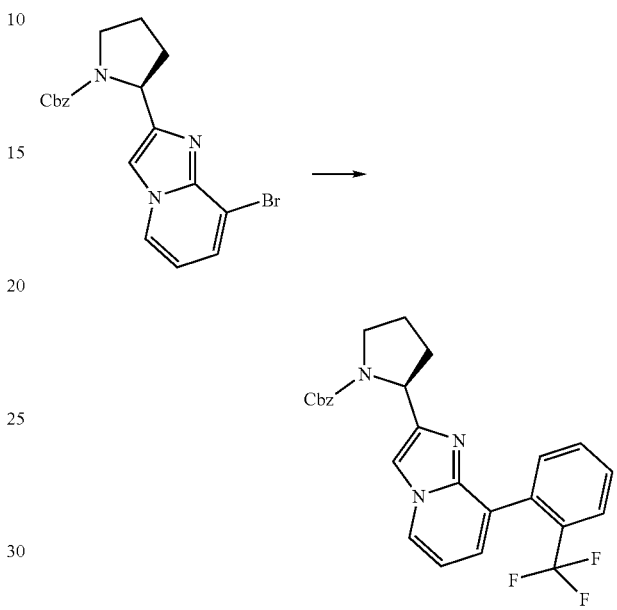

Following procedures of example 14, (S)-benzyl-2-(8-bromoimidazo[1,2-a]pyridin-2-yl)pyrrolidine-1-carboxylate (0.250 g, 0.62 mmol), 2-trifluoromethylphenyl boronic acid (0.1538 g, 0.81 mmol), potassium carbonate (0.1292 g, 0.93 mmol), and tetrakis(triphenylphosphine)palladium(0) (0.0360 g, 0.03 mmol) produced the crude material which was adsorbed onto silica gel and purified by flash chromatography (4 g $SiO_2$, 0-100% ethyl acetate in hexanes) to give (2S)-benzyl-2-(8-(2-(trifluoromethyl)phenyl)imidazo[1,2-a]pyridin-2-yl)pyrrolidine-1-carboxylate (0.264 g, 0.57 mmol, 70%).

Example 17

(2S)-benzyl-2-(8-(2-methoxyphenyl)imidazo[1,2-a]pyridin-2-yl)pyrrolidine-1-carboxylate

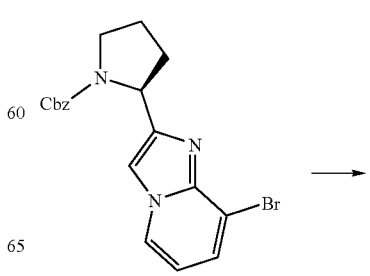

-continued

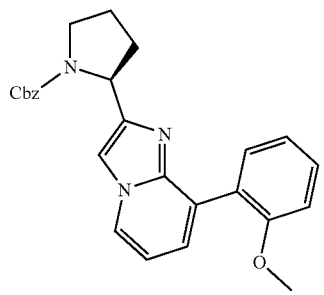

Following the procedures of example 14, (S)-benzyl-2-(8-bromoimidazo[1,2-a]pyridin-2-yl)pyrrolidine-1-carboxylate (0.250 g, 0.62 mmol), 2-methoxyphenyl boronic acid (0.1231 g, 0.81 mmol), potassium carbonate (0.1292 g, 0.93 mmol), and tetrakis(triphenylphosphine)-palladium(0) (0.0360 g, 0.03 mmol) produced the crude material which was adsorbed onto silica gel and purified by flash chromatography (4 g SiO$_2$, 0-100% ethyl acetate in hexanes) to give (2S)-benzyl-2-(8-(2-methoxyphenyl)imidazo[1,2-a]pyridin-2-yl)pyrrolidine-1-carboxylate (0.269 g, 0.63 mmol, 78%).

Example 18

(2S)-benzyl-2-(8-(naphthalen-1-yl)imidazo[1,2-a]pyridin-2-yl)pyrrolidine-1-carboxylate

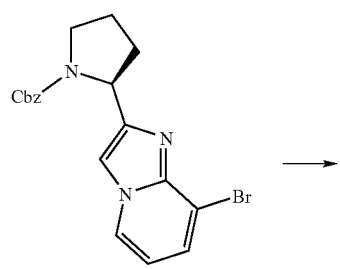

Following the procedures of example 14, (S)-benzyl-2-(8-bromoimidazo[1,2-a]pyridin-2-yl)pyrrolidine-1-carboxylate (0.250 g, 0.62 mmol), 1-napthyl boronic acid (0.1405 g, 0.82 mmol), potassium carbonate (0.1340 g, 0.97 mmol), and tetrakis(triphenylphosphine)palladium(0) (0.0430 g, 0.04 mmol) produced the crude material which was adsorbed onto silica gel and purified by flash chromatography (4 g SiO$_2$, 0-50% ethyl acetate in hexanes) to give (2S)-benzyl 2-(8-(naphthalen-1-yl)imidazo[1,2-a]pyridin-2-yl)pyrrolidine-1-carboxylate (0.183 g, 0.41 mmol, 66%).

Example 19

(2S)-benzyl-2-(8-(2-fluorophenyl)imidazo[1,2-a]pyridin-2-yl)pyrrolidine-1-carboxylate

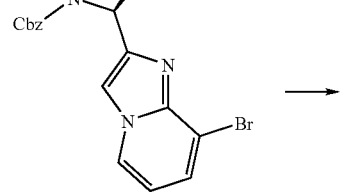

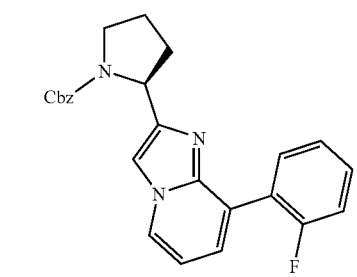

Following the procedures of example 14, (S)-benzyl-2-(8-bromoimidazo[1,2-a]pyridin-2-yl)pyrrolidine-1-carboxylate (0.2489 g, 0.62 mmol), 2-fluorophenyl boronic acid (0.1217 g, 0.87 mmol), potassium carbonate (0.1449 g, 1.05 mmol), and tetrakis(triphenylphosphine)-palladium(0) (0.0532 g, 0.05 mmol) produced the crude material which was adsorbed onto silica gel and purified by flash chromatography (4 g SiO$_2$, 0-60% ethyl acetate in hexanes) to give (2S)-benzyl 2-(8-(2-fluorophenyl)imidazo[1,2-a]pyridin-2-yl)pyrrolidine-1-carboxylate (0.62 mmol, 100%).

Example 20

(S)-benzyl-2-(6-methyl-8-phenylimidazo[1,2-a]pyridin-2-yl)pyrrolidine-1-carboxylate

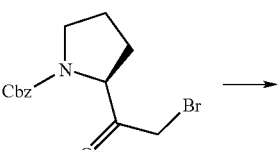

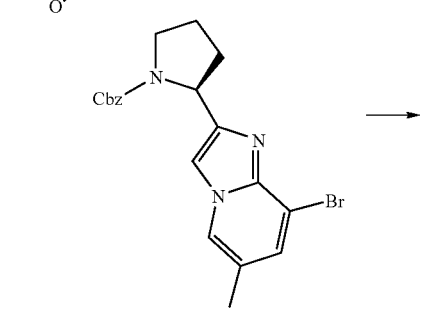

-continued

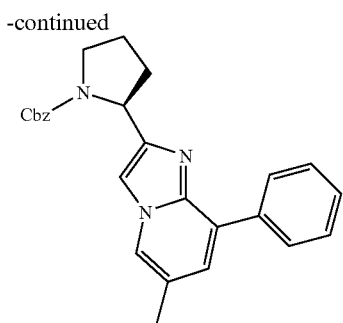

Following the procedures of example 14, (S)-benzyl-2-(2-bromoacetyl)pyrrolidine-1-carboxylate (0.295 g, 0.90 mmol) and 2-amino-3-bromo-5-methylpyridine (0.1765 g, 0.94 mmol), produced the crude material which was adsorbed onto silica gel and purified by flash chromatography (12 g SiO$_2$, 0-50% ethyl acetate in hexanes) to give (S)-benzyl-2-(8-bromo-6-methylimidazo[1,2-a]pyridin-2-yl)pyrrolidine-1-carboxylate (0.165 g, 0.40 mmol, 44%).

(S)-benzyl-2-(8-bromo-6-methylimidazo[1,2-a]pyridin-2-yl)pyrrolidine-1-carboxylate (0.165 g, 0.40 mmol), phenyl boronic acid (0.0740 g, 0.61 mmol), potassium carbonate (0.1449 g, 0.65 mmol), and tetrakis(triphenylphosphine)palladium(0) (0.0351 g, 0.03 mmol) produced the crude material which was adsorbed onto silica gel and purified by flash chromatography (4 g SiO$_2$, 0-50% ethyl acetate in hexanes) to give (S)-benzyl-2-(6-methyl-8-phenylimidazo[1,2-a]pyridin-2-yl)pyrrolidine-1-carboxylate (0.40 mmol, 100%).

Example 21

(S)-benzyl-2-(7-methyl-8-phenylimidazo[1,2-a]pyridin-2-yl)pyrrolidine-1-carboxylate

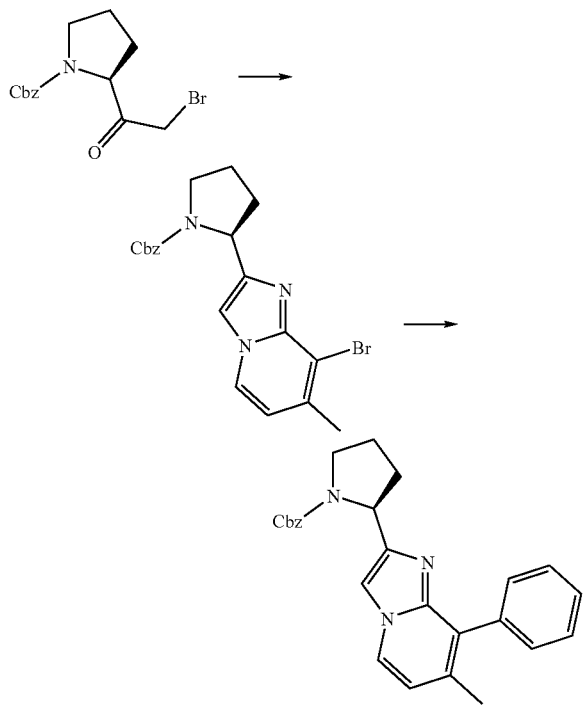

Following the procedures of example 14, (S)-benzyl-2-(2-bromoacetyl)pyrrolidine-1-carboxylate (0.400 g, 1.23 mmol) and 2-amino-3-bromo-4-methylpyridine (0.2344 g, 1.25 mmol), produced the crude material which was adsorbed onto silica gel and purified by flash chromatography (12 g SiO$_2$, 0-50% ethyl acetate in hexanes) to give (S)-benzyl-2-(8-bromo-7-methylimidazo[1,2-a]pyridin-2-yl)pyrrolidine-1-carboxylate (0.239 g, 0.58 mmol, 47%).

(S)-benzyl 2-(8-bromo-7-methylimidazo[1,2-a]pyridin-2-yl)pyrrolidine-1-carboxylate (0.239 g, 0.58 mmol), phenyl boronic acid (0.0936 g, 0.77 mmol), potassium carbonate (0.1496 g, 1.08 mmol), and tetrakis(triphenylphosphine)palladium(0) (0.0534 g, 0.05 mmol) produced the crude material which was adsorbed onto silica gel and purified by flash chromatography (4 g SiO$_2$, 0-60% ethyl acetate in hexanes) to give (S)-benzyl 2-(7-methyl-8-phenylimidazo[1,2-a]pyridin-2-yl)pyrrolidine-1-carboxylate (0.58 mmol, 100%).

Example 22

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells. MLXBIR3SG sequence:

(SEQ ID NO.: 1)
MGSSHHHHHHSSGLVPRGSHMLETEEEEEGAGATLSRGPAFPGMGSEEL

RLASFYDWPLTAEVPPELLAAAGFFHTGHQDKVRCFFCYGGLQSWKRGDD

PWTEHAKWFPGCQFLLRSKGQEYINNIHLTHSL

TR-FRET Peptide Binding Assay

Time-Resolved Fluorescence Resonance Energy Transfer competition experiments are performed on the Wallac Victor2 Multilabeled Counter Reader (Perkin Elmer Life and Analytical Sciences, Inc.) according to the procedures of Kolb et al (Journal of Biomolecular Screening, 1996, 1(4):203). A reagent cocktail containing 300 nM his-tagged MLXBIR3SG; 200 nM biotinylated SMAC peptide (AVPI); 5 μg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail is incubated at room temperature for 30 minutes. After incubation, the cocktail is added to 1:3 serial dilutions of an antagonist compound (starting concentration of 50 μM) in 384-well black FIA plates (Greiner Bio-One, Inc.). After a 90 minute incubation at room temperature, the fluorescence is read with filters for the excitation of europium (340 nm) and for the emission wavelengths of europium (615 nm) and a allophycocyanin (665 nm). Antagonist data is calculated as a ratio of the emission signal of allophycocyanin at 665 nm to that of the emission of europium at 615 nm (these ratios are multiplied by a factor of 10,000 for ease of data manipulation). The resulting values are plotted as a function of antagonist concentration and fit to a 4-parameter equation using Kaleidograph software (Synergy Software, Reading, Pa.). Indications of antagonist potency are determined from the $IC_{50}$ values.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S. (2000) in *Proceedings of SPIE: In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 μM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-$NH_2$ (AVP-diPhe-FAM) at 5 nM final concentration.

96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 μM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.). Inhibition constants ($K_i$) for the antagonists were determined from the $IC_{50}$ values. Compounds of the invention that were tested in this assay exhib-

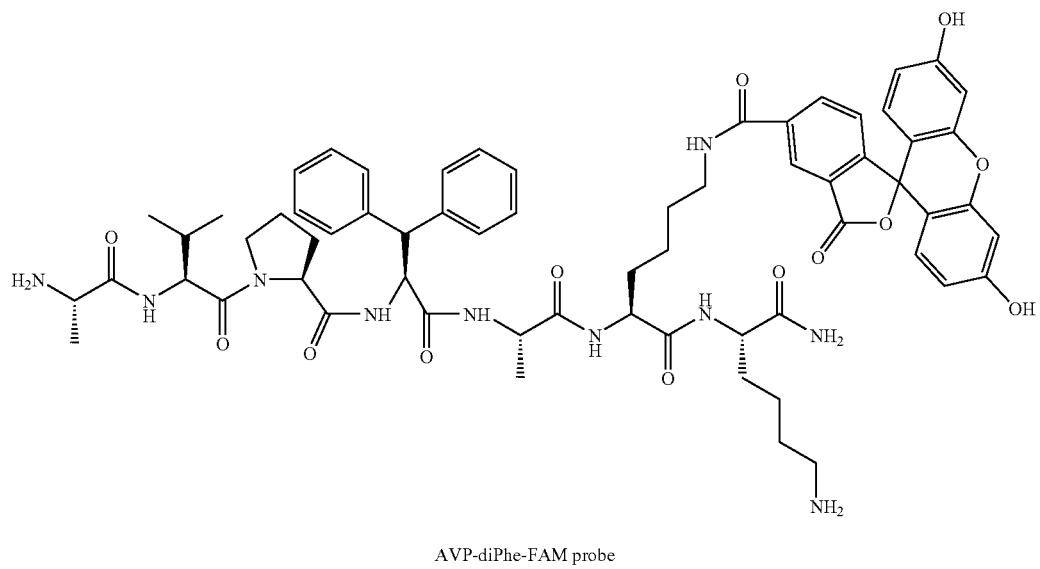

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in ited a Ki or less than 50 μM. For example, compound 7 had a Ki of 18.917, compound 20 had a Ki of 1.8312, compound 1 had an Ki of 0.0891 and compound 8 had a Ki of 2.3067.

---

I claim:

1. A compound of formula (I)

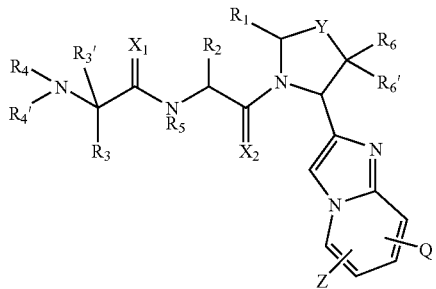

wherein $X_1$ and $X_2$ are each independently O or S;

Y is a bond, $(CR_7R_7)_m$, O or S;

Z is H, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)—;

Q is H, halogen, hydroxyl, carboxyl, amino, nitro, cyano, alkyl, a carbocycle or a heterocycle; wherein said alkyl, carbocycle and heterocycle is optionally substituted with one or more hydroxyl, alkoxy, acyl, halogen, mercapto, oxo, carboxyl, acyl, optionally substituted alkyl, amino, cyano, nitro, amidino, guanidino an optionally substituted carbocycle or an optionally substituted heterocycle; and wherein one or more $CH_2$ or CH groups of an alkyl is optionally replaced with —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —NR$_8$—C(NH)—NR$_8$—, —NR$_8$—C(NH)—, —C(O)—O— or —O—C(O)—;

$R_1$ is H, OH or alkyl; or $R_1$ and $R_2$ together form a 5-8 member heterocycle;

$R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, acyl, alkoxy, alkylthio, sulfonyl, amino and nitro, wherein said alkyl, acyl, alkoxy, alkylthio and sulfonyl are optionally substituted with hydroxy, mercapto, halogen, amino, alkoxy, hydroxyalkoxy and alkoxyalkoxy;

$R_3$ is H or alkyl optionally substituted with halogen or hydroxyl; or $R_3$ and $R_4$ together form a 3-6 heterocycle;

$R_3'$ is H, or $R_3$ and $R_3'$ together form a 3-6 carbocycle;

$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle;

$R_5$ is H or alkyl;

$R_6$, and $R_6'$ are each independently H, alkyl, aryl or aralkyl;

$R_7$ is H, cyano, hydroxyl, mercapto, halogen, nitro, carboxyl, amidino, guanidino, alkyl, a carbocycle, a heterocycle or -U-V; wherein U is —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, C(NH)—NR$_8$—, —NR$_8$—C(NH)—, —C(O)—O— or —O—C(O)— and V is alkyl, a carbocycle or a heterocycle; and wherein one or more $CH_2$ or CH groups of an alkyl is optionally replaced with —O—, —S—, —S(O)—, S(O)$_2$, —N(R$_8$)—, —C(O)—, —C(O)—NR$_8$—, —NR$_8$—C(O)—, —SO$_2$—NR$_8$—, —NR$_8$—SO$_2$—, —NR$_8$—C(O)—NR$_8$—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle;

$R_8$ is H, alkyl, a carbocycle or a heterocycle wherein one or more $CH_2$ or CH groups of said alkyl is optionally replaced with —O—, —S—, —S(O)—, S(O)$_2$, —N(R$_8$), or —C(O)—; and said alkyl, carbocycle and heterocycle is optionally substituted with hydroxyl, alkoxy, acyl, halogen, mercapto, oxo (═O), carboxyl, acyl, halo-substituted alkyl, amino, cyano nitro, amidino, guanidino an optionally substituted carbocycle or an optionally substituted heterocycle; and m is 0 to 4.

2. The compound of claim 1, wherein Z is H, halogen or alkyl.

3. The compound of claim 1, wherein Y is $CH_2$.

4. The compound of claim 1, wherein Q is a carbocycle or heterocycle optionally substituted with alkyl, a carbocycle or a heterocycle; wherein any alkyl, carbocycle or heterocycle is optionally substituted with halogen, amino, hydroxyl, mercapto, carboxyl, alkoxy, alkoxyalkoxy, hydroxyalkoxy, alkylthio, acyloxy, acyloxyalkoxy, alkylsulfonyl, alkylsulfonylalkyl, alkylsulfinyl, and alkylsulfinylalkyl; and wherein one or more $CH_2$ or CH groups of any foregoing alkyl is optionally replaced with —O—, —S—, —S(O)—, $S(O)_2$, —N($R_8$)—, —C(O)—, —C(O)—$NR_8$—, —$NR_8$—C(O)—, —$SO_2$—$NR_8$—, —$NR_8$—$SO_2$-, —$NR_8$—C(O)—$NR_8$—, —$NR_8$—C(NH)—$NR_8$—, —$NR_8$—C(NH)—, —C(O)—O— or —O—C(O)—;

5. The compound of claim 1, wherein Q is a carbocycle or heterocycle selected from the group consisting of IIIa-IIIs:

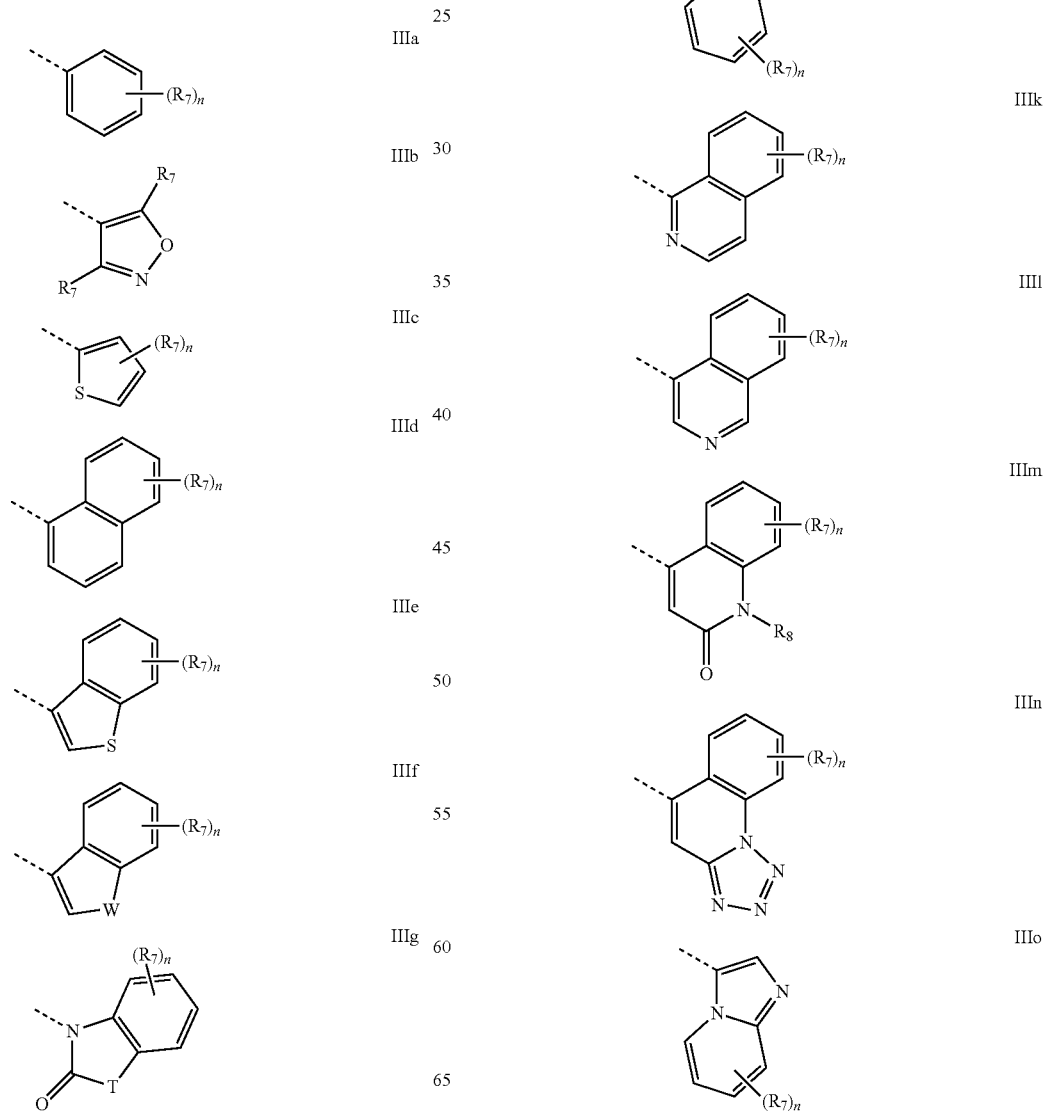

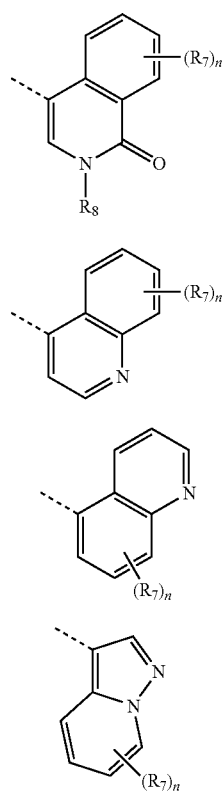

wherein n is 1-4; T is O, S, $NR_8$ or $CR_7R_7$; and W is O, $NR_8$ or $CR_7R_7$.

6. The compound of claim 1, wherein $R_1$ is H.

7. The compound of claim 1, wherein $R_2$ is alkyl, cycloalkyl or a heterocycle.

8. The compound of claim 1, wherein $R_2$ is selected from the group consisting of t-butyl, isopropyl, cyclohexyl, tetrahydropyran-4-yl, N-methylsulfonylpiperidin-4-yl, tetrahydrothiopyran-4-yl, tetrahydrothiopyran-4-yl (in which the S is in oxidized form SO or $SO_2$), cyclohexan-4-one, 4-hydroxycyclohexane, 4-hydroxy-4-methylcyclohexane, 1-methyl-tetrahydropyran-4-yl, 2-hydroxyprop-2-yl, but-2-yl, thiophen-3-yl, piperidin-4-yl, N-acetylpiperidin-4-yl, N-hydroxyethylpiperidin-4-yl, N-(2-hydroxyacetyl)piperidin-4-yl, N-(2-methoxyacetyl)piperidin-4-yl, pyridin-3-yl, phenyl and 1-hydroxyeth-1-yl.

9. The compound of claim 1, wherein $R_3$ is methyl.

10. The compound of claim 1, wherein $R_4$ is H or methyl, and $R_4'$ is H.

11. The compound of claim 1, wherein $R_5$ is H.

12. The compound of claim 1, wherein $R_6$ and $R_6'$ are both H.

13. The compound of claim 1, wherein $X_1$ and $X_2$ are both O.

14. The compound of claim 2, wherein $R_1$ is H; $R_2$ is isopropyl, t-butyl, cyclohexyl or pyran; $R_3$ is methyl; $R_3$, is H; $R_4$ is methyl, $R_4'$ is H; $R_5$ is H; $X_1$ and $X_2$ are both O; and $R_6$ and $R_6$, are both H.

* * * * *

UNITED STATES PATENT AND TRADEMARK OFFICE
CERTIFICATE OF CORRECTION

| | | |
|---|---|---|
| PATENT NO. | : 8,063,218 B2 | Page 1 of 1 |
| APPLICATION NO. | : 12/520205 | |
| DATED | : November 22, 2011 | |
| INVENTOR(S) | : Michael F. T. Koehler | |

It is certified that error appears in the above-identified patent and that said Letters Patent is hereby corrected as shown below:

In Column 64, line 48, claim 1, please delete "$C(NH)-NR_8$", and insert --$NR_8-C(NH)-NR_8$--.

Signed and Sealed this

Seventeenth Day of January, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Met Gly Ser Ser His His His His His His Ser Ser Gly Leu Val
1               5                   10                  15

Pro Arg Gly Ser His Met Leu Glu Thr Glu Glu Glu Glu Glu
                20                  25                  30

Gly Ala Gly Ala Thr Leu Ser Arg Gly Pro Ala Phe Pro Gly Met
                35                  40                  45

Gly Ser Glu Glu Leu Arg Leu Ala Ser Phe Tyr Asp Trp Pro Leu

-continued

```
                  50                  55                  60
Thr Ala Glu Val Pro Pro Glu Leu Leu Ala Ala Gly Phe Phe
                  65                  70                  75
His Thr Gly His Gln Asp Lys Val Arg Cys Phe Phe Cys Tyr Gly
                  80                  85                  90
Gly Leu Gln Ser Trp Lys Arg Gly Asp Asp Pro Trp Thr Glu His
                  95                 100                 105
Ala Lys Trp Phe Pro Gly Cys Gln Phe Leu Leu Arg Ser Lys Gly
                 110                 115                 120
Gln Glu Tyr Ile Asn Asn Ile His Leu Thr His Ser Leu
                 125                 130
```